US011393578B2

(12) United States Patent
Aydelotte et al.

(10) Patent No.: US 11,393,578 B2
(45) Date of Patent: Jul. 19, 2022

(54) METHOD AND SYSTEM TO FACILITATE PATIENT CARE

(71) Applicant: BUELLER RNDS, INC., Austin, TX (US)

(72) Inventors: Jayson Aydelotte, Austin, TX (US); John Sabra, Austin, TX (US)

(73) Assignee: BUELLER RNDS, INC., Austin, TX (US)

( * ) Notice: Subject to any disclaimer, the term of this patent is extended or adjusted under 35 U.S.C. 154(b) by 302 days.

(21) Appl. No.: 16/468,005

(22) PCT Filed: Dec. 20, 2017

(86) PCT No.: PCT/US2017/067702
§ 371 (c)(1),
(2) Date: Jun. 10, 2019

(87) PCT Pub. No.: WO2018/119134
PCT Pub. Date: Jun. 28, 2018

(65) Prior Publication Data
US 2020/0013497 A1  Jan. 9, 2020

Related U.S. Application Data

(60) Provisional application No. 62/589,010, filed on Nov. 21, 2017, provisional application No. 62/438,845, filed on Dec. 23, 2016.

(51) Int. Cl.
*G16H 40/20* (2018.01)
*G16H 10/60* (2018.01)
(52) U.S. Cl.
CPC .............. *G16H 40/20* (2018.01); *G16H 10/60* (2018.01)

(58) Field of Classification Search
None
See application file for complete search history.

(56) References Cited

U.S. PATENT DOCUMENTS 6,876,303 B2   4/2005   Reeder et al.
6,982,639 B2   1/2006   Brackett et al.
(Continued)

FOREIGN PATENT DOCUMENTS

CN   204576580   8/2015
CN   105373871   3/2016
(Continued)

OTHER PUBLICATIONS

Hit Em Up App, How to Send Mass Text on iPhone (Personally and Privately), Jun. 17, 2017, https://www.youtube.com/watch?v=jqRZ3dNRHk8 (Year: 2017).*
(Continued)

*Primary Examiner* — Devin C Hein
(74) *Attorney, Agent, or Firm* — Trop, Pruner & Hu, P.C.

(57) ABSTRACT

An embodiment includes displaying to a physician at least one of: (a)(i) a hospital floor map, (a)(ii) a first patient identifier, and (a)(iii) a second patient identifier, wherein (b)(i) the map displays first and second rooms of the hospital floor, (b)(ii) a first patient is assigned to the first room and the first patient identifier, (b)(iii) a second patient is assigned to the second room and a second patient identifier, and (b)(iv) a first nurse is assigned to the first room and the first patient identifier, (b)(v) and a second nurse is assigned to the second room and the second patient identifier; receiving a selection from the physician, the selection comprising at least one of the displayed first room and the displayed first patient identifier; and sending a communication from the physician to the first nurse, and not the second nurse, in response to receiving the selection.

14 Claims, 41 Drawing Sheets

(56) References Cited

U.S. PATENT DOCUMENTS

| | | |
|---|---|---|
| 7,319,386 B2 | 1/2008 | Collins et al. |
| 7,627,334 B2 | 12/2009 | Cohen et al. |
| 8,135,602 B2 | 3/2012 | Xiao et al. |
| 8,799,021 B2 | 8/2014 | Flanagan et al. |
| 9,147,334 B2 | 9/2015 | Long et al. |
| 9,240,120 B2 | 1/2016 | Girardeau et al. |
| 9,378,485 B2 | 6/2016 | Preiss et al. |
| 9,473,886 B2 | 10/2016 | Katpelly et al. |
| 2004/0128163 A1 | 7/2004 | Goodman et al. |
| 2011/0276396 A1 | 11/2011 | Rathod |
| 2012/0101847 A1 | 4/2012 | Johnson et al. |
| 2012/0278104 A1* | 11/2012 | Traughber ......... G08B 21/0277 705/3 |
| 2012/0290311 A1 | 11/2012 | Tara et al. |
| 2012/0310664 A1 | 12/2012 | Long et al. |
| 2013/0073344 A1 | 3/2013 | Parent |
| 2013/0132116 A1 | 5/2013 | Natarajan |
| 2013/0253951 A1 | 9/2013 | Richter et al. |
| 2013/0262196 A1 | 10/2013 | Scalic |
| 2014/0100873 A1 | 4/2014 | Vaglio et al. |
| 2014/0266642 A1* | 9/2014 | Girardeau ............. G16H 40/20 340/286.07 |
| 2014/0278488 A1* | 9/2014 | Moore .................. G16H 10/60 705/2 |
| 2015/0261918 A1 | 9/2015 | Thornbury, Jr. |
| 2015/0332001 A1 | 11/2015 | Goldfein et al. |
| 2016/0027289 A1 | 1/2016 | Hargis |
| 2016/0277560 A1 | 9/2016 | Gruberman et al. |

FOREIGN PATENT DOCUMENTS

| | | | |
|---|---|---|---|
| JP | 2013158521 | 8/2013 | |
| WO | WO-03058539 A2 * | 7/2003 | ............ G06Q 10/10 |
| WO | 2010150031 | 12/2010 | |
| WO | 2012150602 | 11/2012 | |

OTHER PUBLICATIONS

International Searching Authority, "Notification of Transmittal of the International Search Report and the Written Opinion of the International Searching Authority," dated Apr. 16, 2018, in International application No. PCT/US2017/067702.

Coyle, et al., "Sensor Aggregation and Integration in Healthcare Location Based Services", 2006, 4 pages, Pervasive Health Conference and Workshops.

Yao, et al., "Using Ontology to Support Context Awareness in Healthcare", Dec. 14-15, 2009, 6 pages, Proceedings of the 19th Workshop on Information Technologies and Systems, Phoenix, AZ, USA.

Ward, et al., "A real-time locating system observes physician time-motion patterns during walk-rounds: a pilot study." 2014, 7 pages, BMC Medical Education 14.1.

Peçel, Enhanced Hole Punching for RSSI Location Tracking in Hospitals, Mar. 2008, 53 pages, The Middle East Technical University.

Andon, Usability Analysis of Wireless Tablet Computing in an Academic Emergency Department, May 11, 2004, 57 pages, Capstone Project.

* cited by examiner

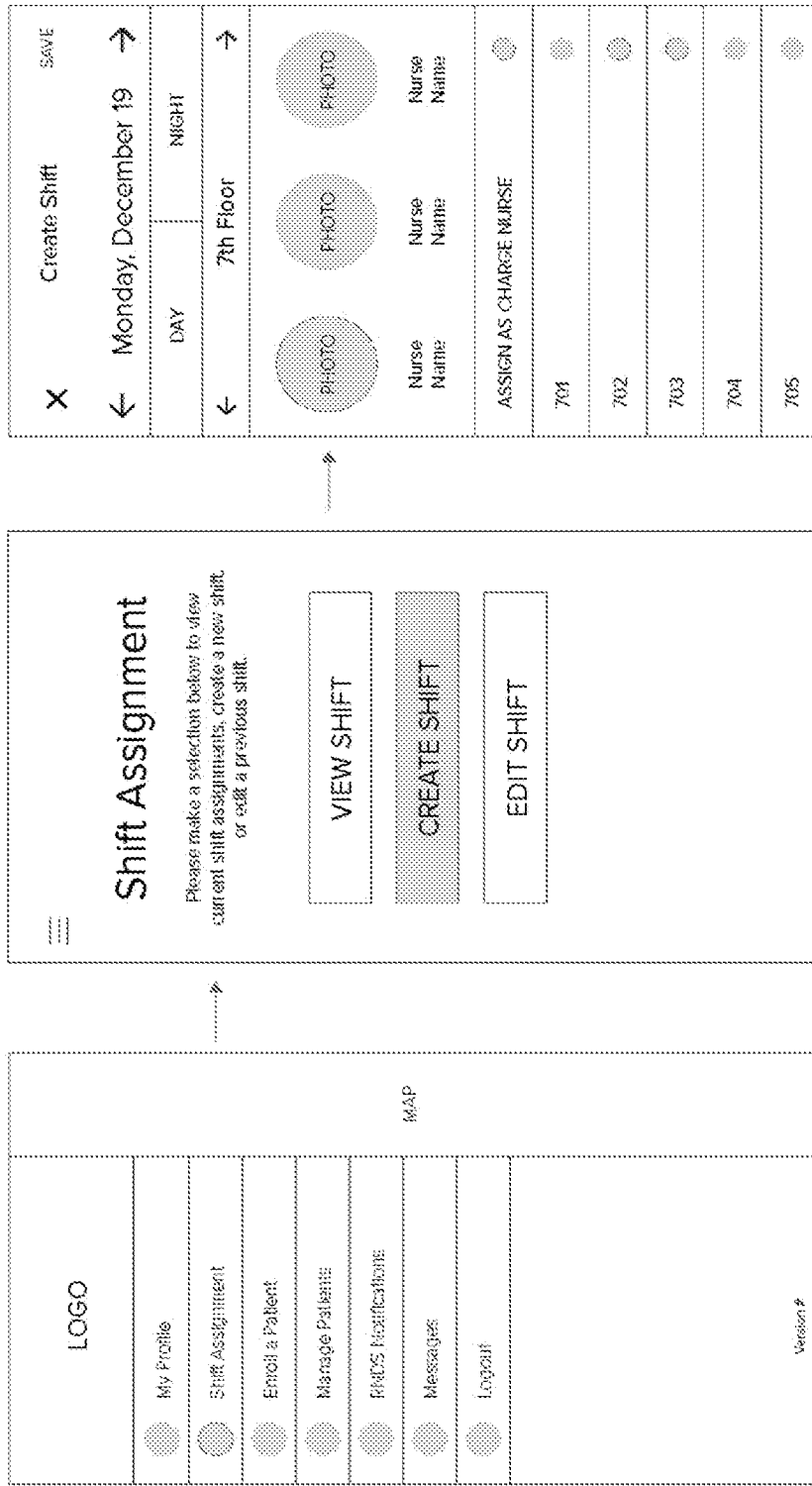

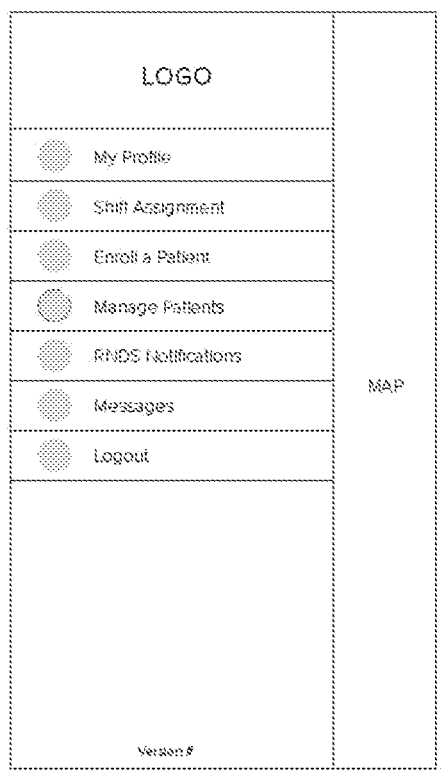
Figure 33
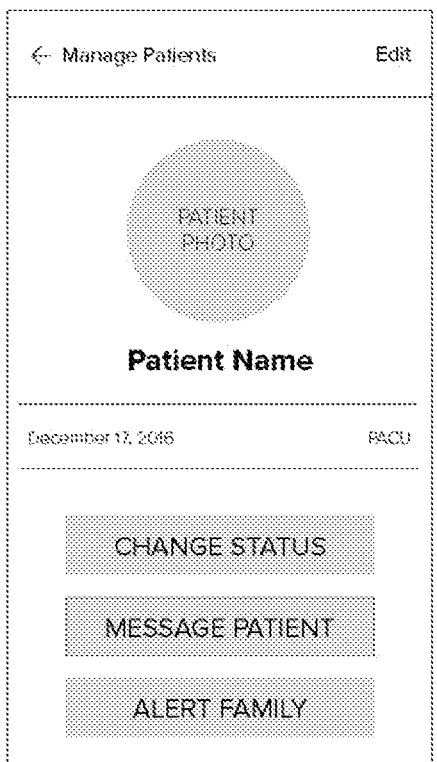
Figure 34
Figure 35
Figure 36

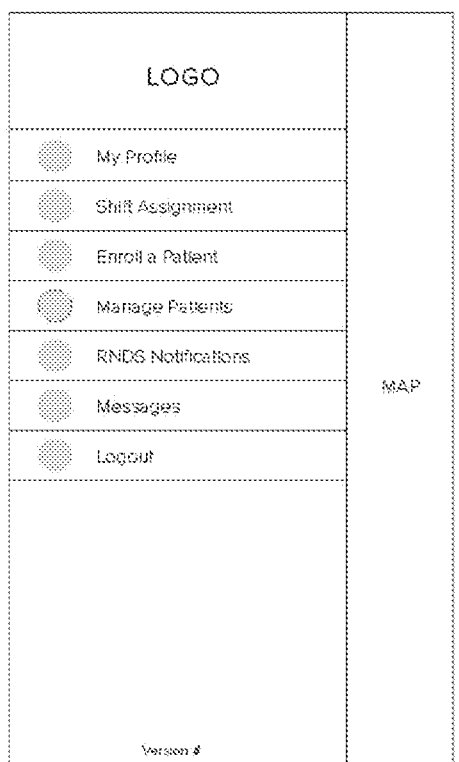
Figure 37
Figure 38
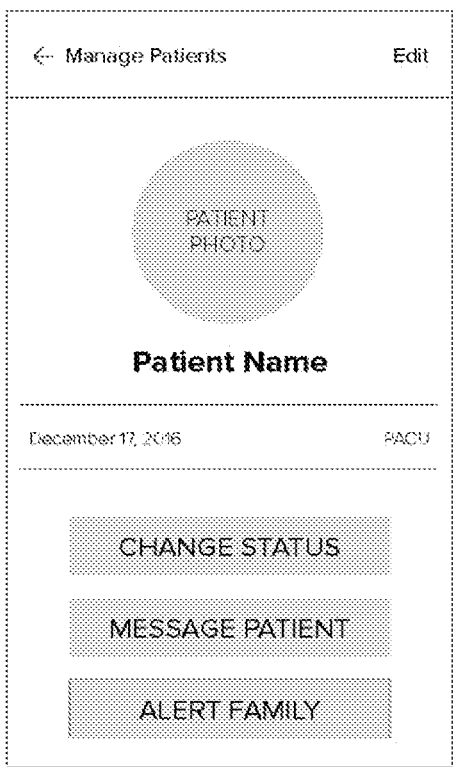
Figure 39
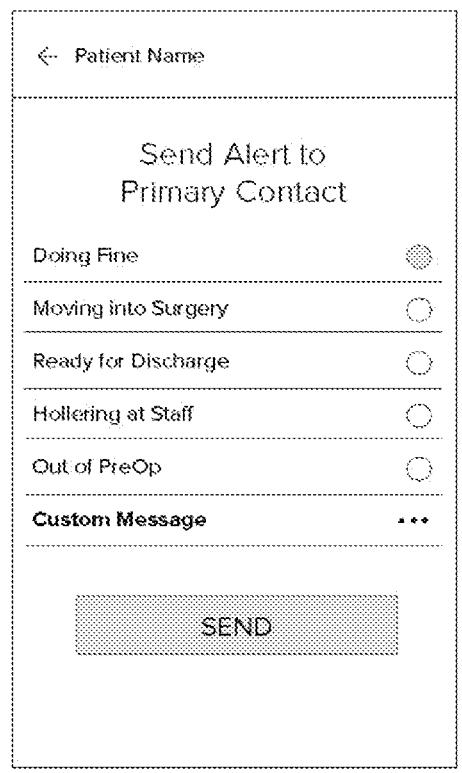
Figure 40

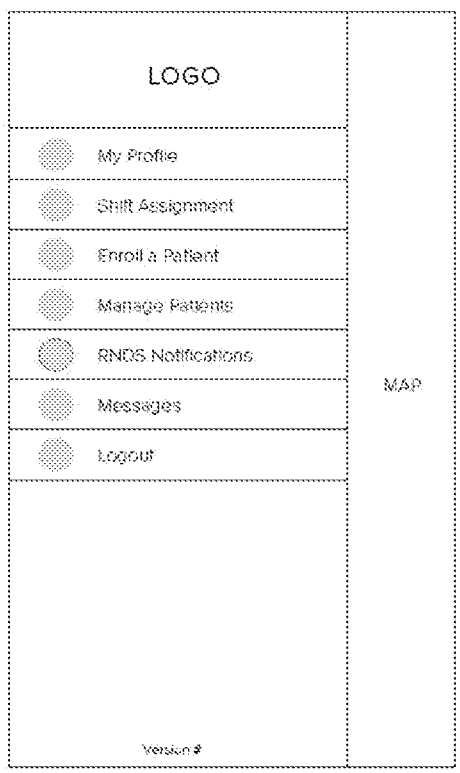
Figure 46
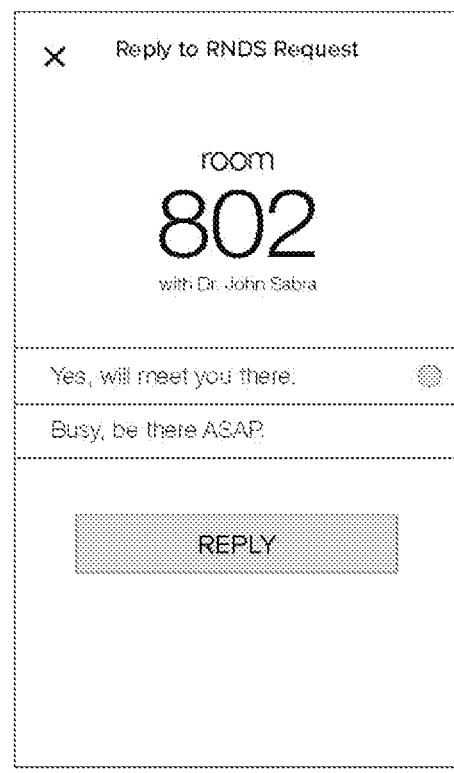
Figure 47
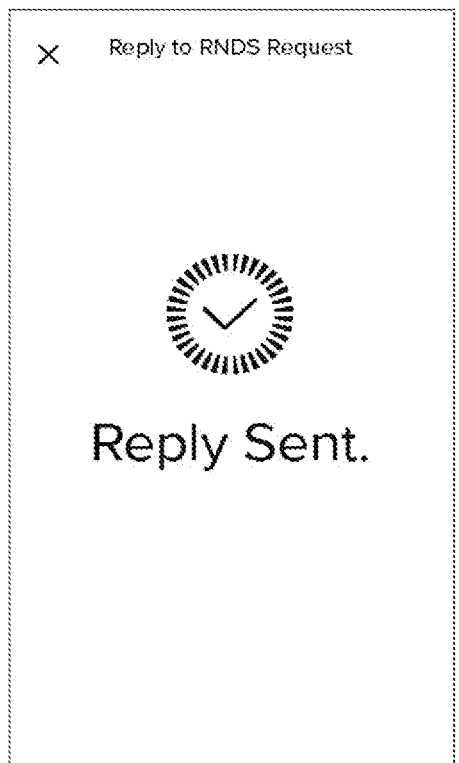
Figure 48
| | RNDS Notificatons | |
|---|---|---|
| DOCTOR | ROOM | WHEN |
| Dr. Name | 180 | 4 days ago |
| Dr. Name | 569 | 3 days ago |
| Dr. Name | 809 | Today |
| Dr. Name | 559 | 4 days ago |
| Dr. Name | 569 | 3 days ago |
| Dr. Name | 778 | Today |
| Dr. Name | 778 | 4 days ago |
| Dr. Name | 119 | 3 days ago |
| Dr. Name | 259 | Today |
| Dr. Name | 648 | 4 days ago |
| Dr. Name | 548 | 3 days ago |
| Dr. Name | 189 | Today |
Figure 49

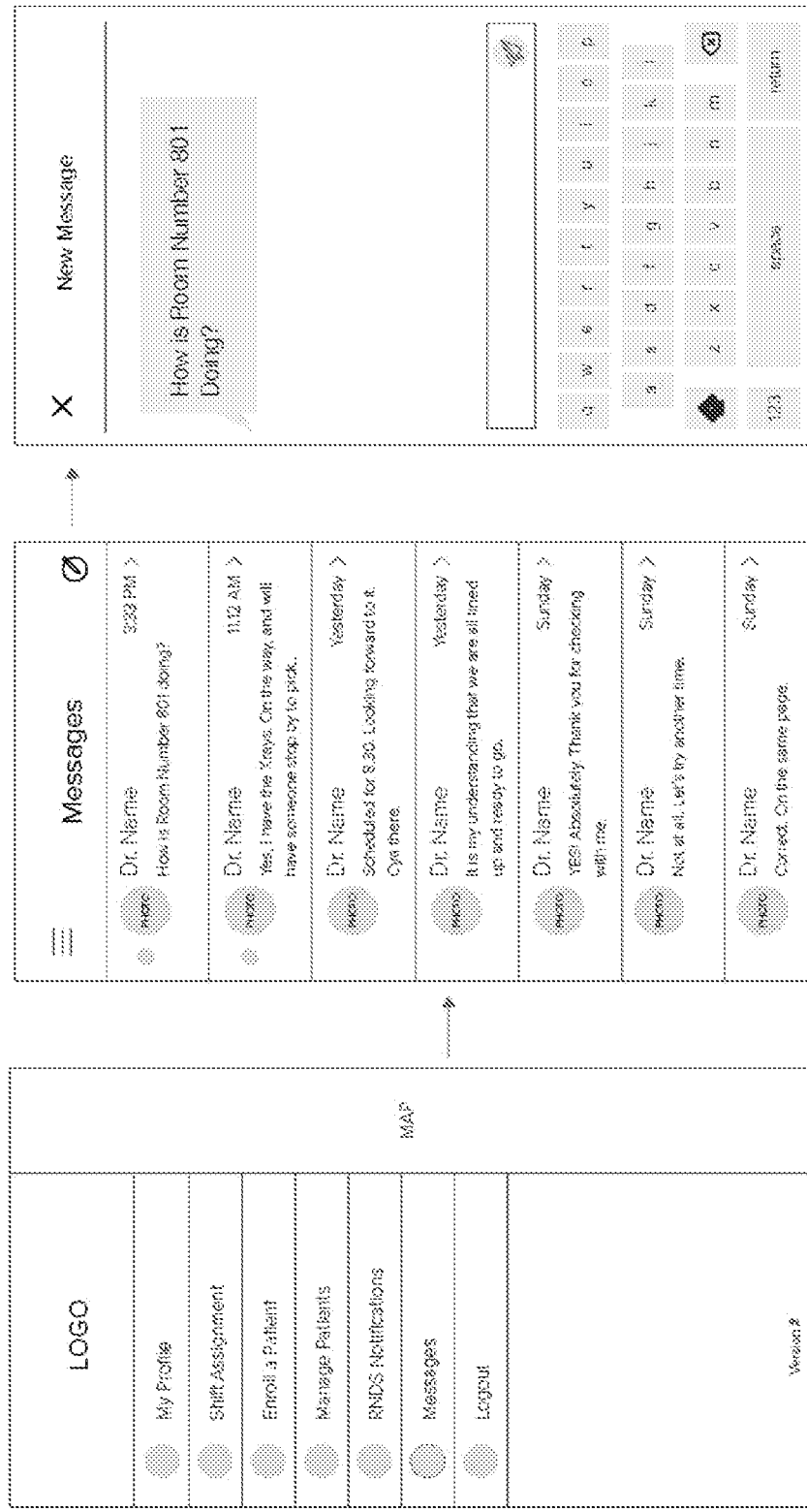

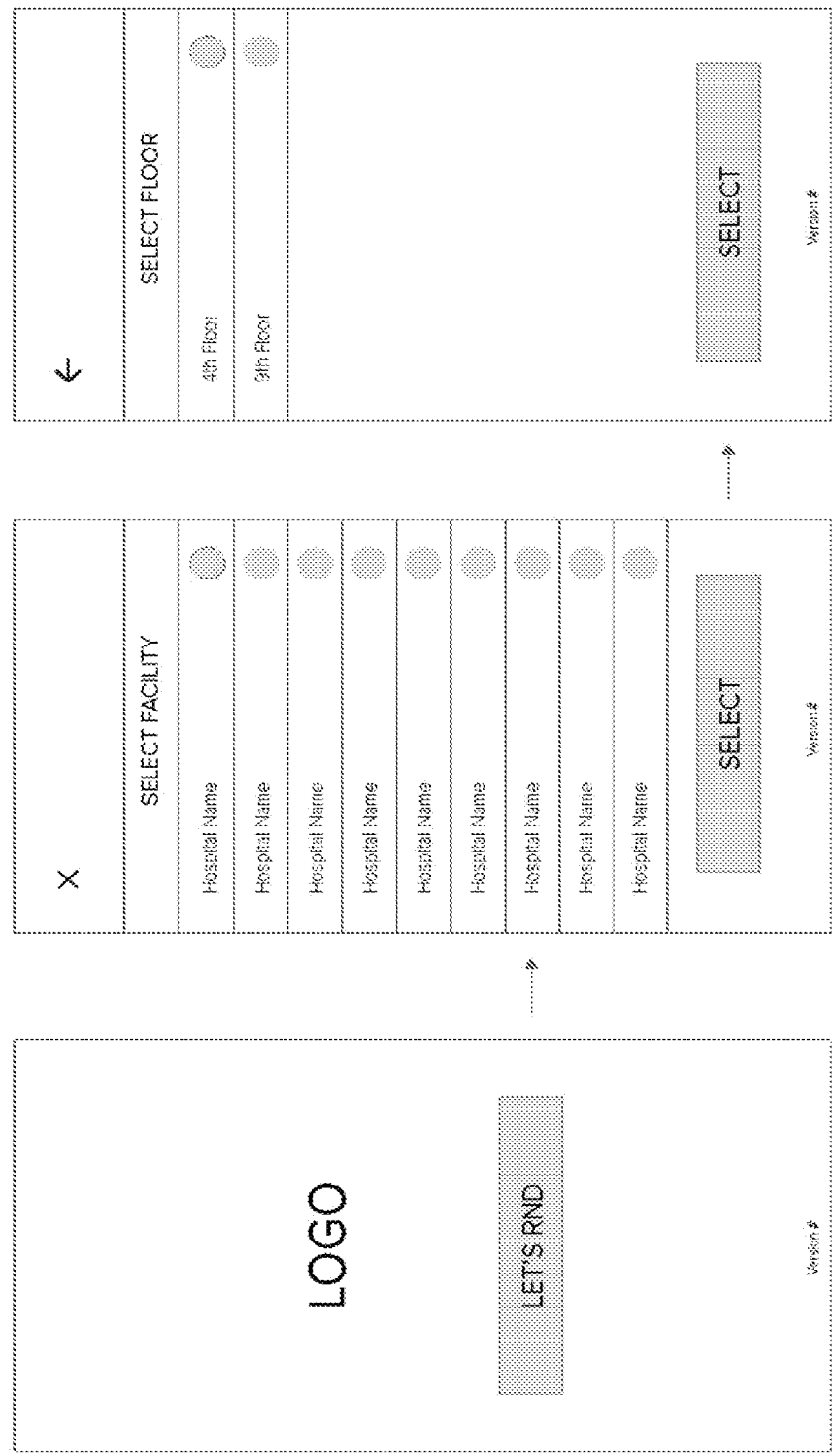

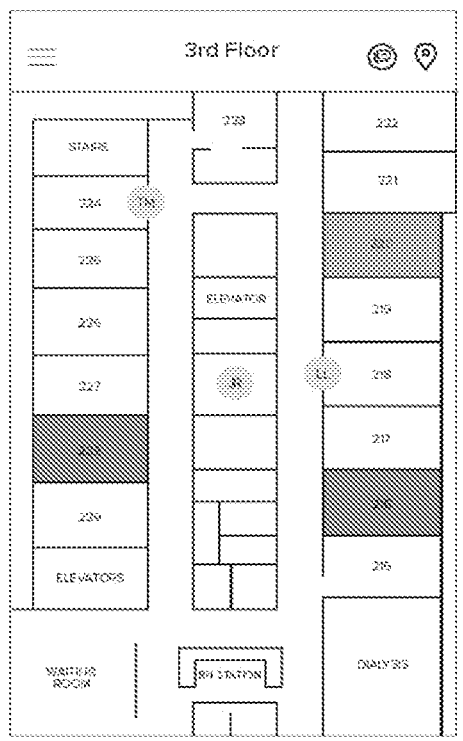
Figure 61
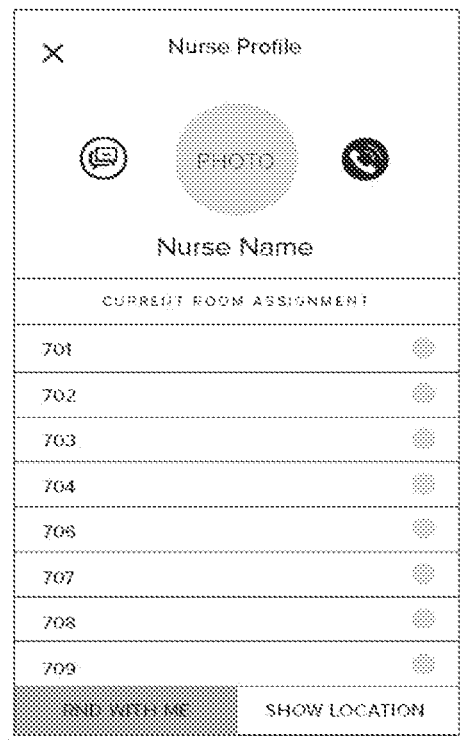
Figure 62
Figure 63
Figure 64

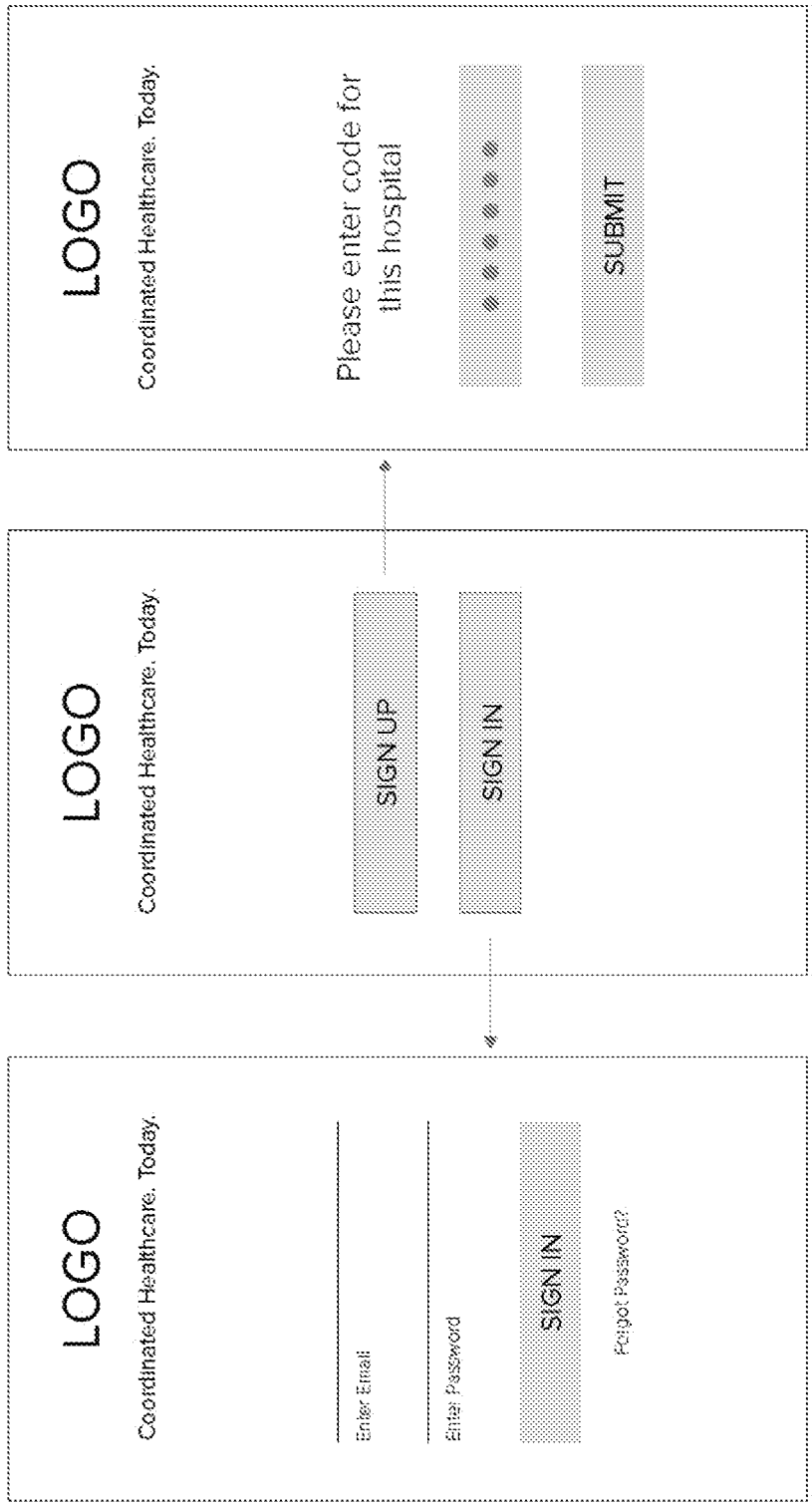

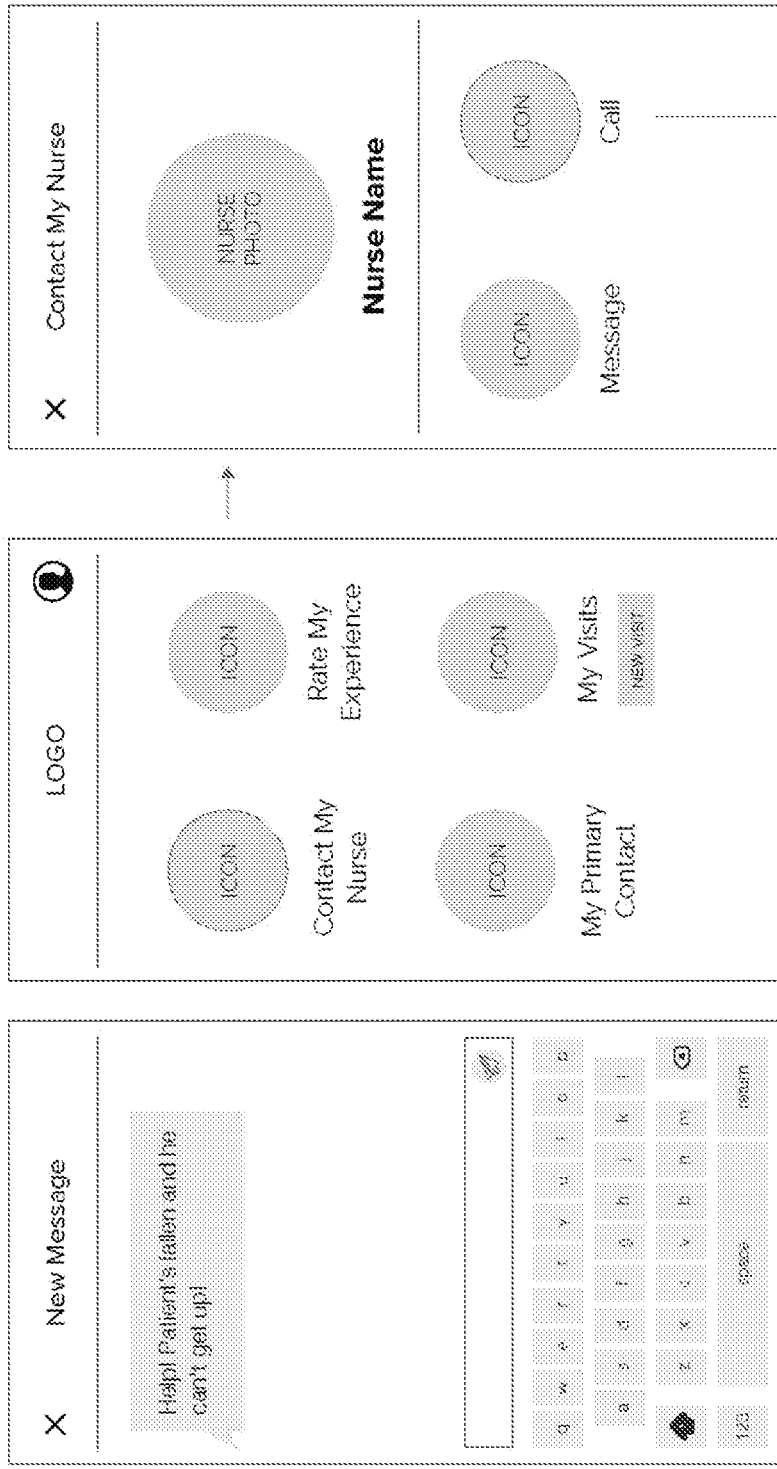

Initial setup
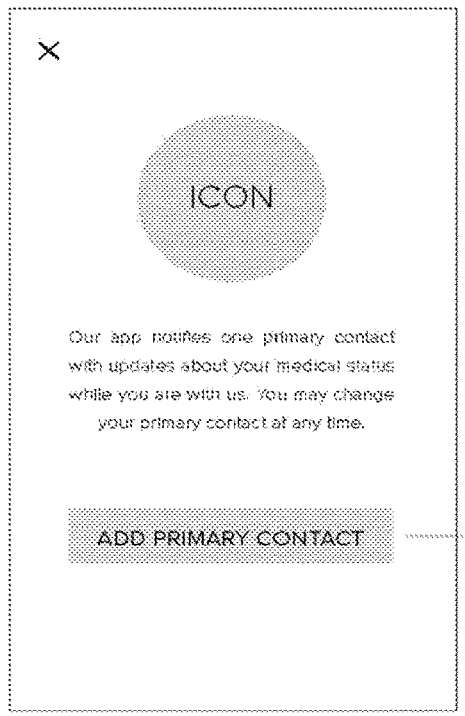
Figure 89
Figure 90
Change family member contact afer initial setup
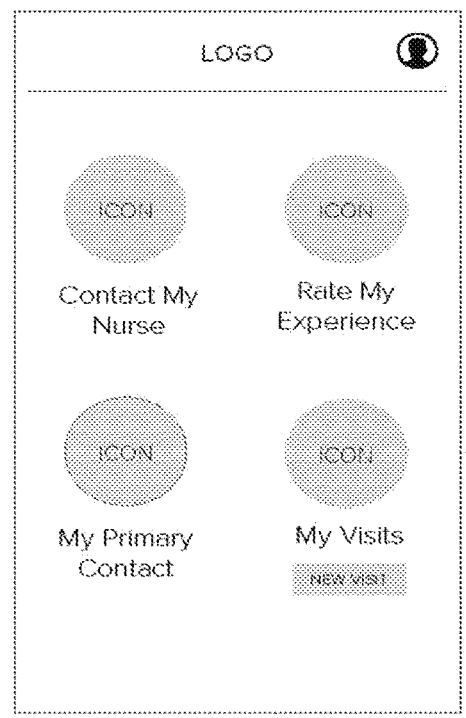
Figure 91
Figure 92

```javascript
function sanatizeWifi(wifiReadings) {

//Combine readings from the same access point even if the readings are on different channels
    var newmap = getBSSIDNames(wifiReadings).reduce((previous,elem)=>{
        var key = elem.substring(0,elem.length-1)

previous[key] = previous[key] == null ? [] : previous[key]
        previous[key].push(wifiReadings[elem])

return previous
    },{})

//Average the readings per access point
    return getWifiBSSIDNames(newmap).reduce((previous,key) =>{ var average = newmap[key].reduce((s,v)=>{
            return s+v;
        },0) / newmap[key].length previous[key] = average return previous
    },{})

} function sanatizeModel(model) {
    //Combine model readings from the same access point even readings across different channels.
    return getLocationsInModel(model).reduce((previous,location)=>{
        var readings = model[location]
        var newmap = sanatizeWifi(readings)
        previous[location] = newmap
        return previous
    },{})

}

//Load the location models
var models = {
    '1' : sanatizeModel(require('facility_1_model.json')),
    '2' : sanatizeModel(require('facility_2_model.json')),
}

/**
 * Returns a random number between min (inclusive) and max (exclusive)
 */
function getRandomArbitrary(min, max) {
    return Math.random() * (max - min) + min;
```

/**
 * Returns a random integer between min (inclusive) and max (inclusive)
 * Using Math.round() will give you a non-uniform distribution!
 */
function getRandomInt(min, max) {
    return Math.floor(Math.random() * (max - min + 1)) + min;
}

// Compute the euclidean distance between two vectors of wifi readings.
function computeDistance(reading, average) { var sum = 0
  getBSSIDNames(average).forEach(bssid=>{ if(reading[bssid]!=undefined && reading[bssid]!=null) {
      var val = reading[bssid]
      var avg = average[bssid]

var dif = val - avg
      var sqdif = dif * dif
      sum = sum + sqdif
    }
  })

var result = Math.sqrt(sum)
  return result;
} function findStrongestBSSID(readings) { var tmp = getBSSIDNames(readings).reduce((previous,bssid)=>{
    var val = readings[bssid]
    if(val > previous.max) {
      return {
        max:val,
        bssid:bssid
      }
    } else {
      return previous
    }
  },{max:-105,bssid:null})

return tmp.bssid
```

/**
 * Predict location.
 */
predict(mapId, wifireadings) {

//Clean up the wifi reading to remove extraneous access point that don't help our prediction
model
  var sanatizedReadings = sanatizeWifi(wifireadings)

//Load in the correct model for the floor of interest.
  var model = models[mapId]

//Initialize some state variables that will help us track which location is the best estimate given
the wifi readings.
  var previous_diff = -1
  var best_location_id = -1

//Loop over all the locations in the model to find best match
  getLocationsForMode:(model).forEach(locationId => {

//Load in the average readings for the location
   var average = model[locationId]

//Only consider a location if the strongest access point in the current reading matches strongest
access point for that location.
    if(findStrongestBSSID(sanatizedReadings) === findStrongestBSSID(average)) {
      //Compute the distance between the current reading and the location reading
      var score = computeDistance(sanatizedReadings,average)
      //If the distance is smaller than our previous best estimate then update our estimate.
      if(previous_diff == -1 || score < previous_diff){
        previous_diff = score
        best_location_id = locationId
      }
    }

})

return best_location_id
}
```

FIG. 99C

```
drawMap(forFacility,andFloorNumber);

let nurseLocations = getNurseLocationsFromSever();

drawNurseIconsOnMap(nurseLocations);

while(true) {
  let userTouch = getNextUserTouchEventOnMap()

for each nurseLocation in nurseLocations { if(nurseLocation === userTouch.location) {
       navigateToContactNurseScreen(nurseLocation.nurse)

let contactMethod = getCallOrMessageNurseEvent()
       if(contactMethod === 'call') {
           showPhoneDialerAndPlaceCall();
           waitForCallComplete();
           returnToMap();
           continue;
       } else {
           showTextMessagingScreen();
           let message = acceptTextInput()
           sendMessage(message);
           returnToMap();
           continue;
       }
    }
  }
} int roomNumber = findRoomForTouch(userTouch)

bool isNurseAssigned = checkIfNurseIsAssignedToRoom(roomNumber)

if(isNurseAssigned === true) { bool multipleNurses = checkIfMultipleNursesAssigned(roomNumber)

if(multipleNurses === true) {
        showNurseSelectionScreen();

let selectedNurse = waitForUserToSelectNurse();

navigateToContactNurseScreen(selectedNurse)

let contactMethod = getCallOrMessageNurseEvent()
        if(contactMethod === 'call') {
           showPhoneDialerAndPlaceCall();
           waitForCallComplete();
           returnToMap();
           continue;
        } else {
           showTextMessagingScreen();
           let message = acceptTextInput()
           sendMessage(message);
           returnToMap();
           continue;
        }
    }
}
```

FIG. 101

```
// Update patient status
//Load state variables
const {
patients, selected_patient_index, rooms, selected_room_index,
} = this.state;
//Get the current patient
const patient = patients[selected_patient_index];
//Find the current selected room
const room = rooms[selected_room_index];
//Identify the current visit associated with the patient
const visitId = patients[selected_patient_index].id;
//Create changes to make to the patient and his current visit
const update_visit = {
location_id: rooms[selected_room_index].id,
};
//Prepare a message to send to patient's primary contact.
const message = `Patient is in room ${room.name}`;
//Update the patient record
updateVisit(visitId, vchg).then(() => {
//Ask the nurse if he/she would like to send the primary contact an update/
if(nurseWantsToUpdatePrimaryContact() === true) {
sendSmsToPrimaryContact(patient.patient_id, message)
}else {
return
}
}
```

FIG. 102

METHOD AND SYSTEM TO FACILITATE PATIENT CARE

CROSS-REFERENCE TO RELATED APPLICATION

This application claims priority to U.S. Provisional Patent Application No. 62/589,010 filed on Nov. 21, 2017 and entitled "METHOD AND SYSTEM TO FACILITATE PATIENT CARE". This application claims priority to U.S. Provisional Patent Application No. 62/438,845 filed on Dec. 23, 2016 and entitled "METHOD AND SYSTEM TO FACILITATE PATIENT CARE". The content of each of the above applications is hereby incorporated by reference.

TECHNICAL FIELD

Embodiments of the invention are in the field of medical technology.

BACKGROUND

Health care providers often have a difficult time finding one another within large hospital complexes. Physicians may not know: (1) which nurse is on duty, (2) which nurse is assigned to a particular patient, (3) where a nurse is, and the like. As a result, the process of "rounding" with an entire care team (e.g., a doctor and nurse and possibly other care providers visiting patients) is inefficient as health care providers spend valuable time seeking each other out and/or "round" alone (without other key members of the care team) after failing to find other health care provider team members with which to round.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

FIGS. 4-8 include a process in an embodiment from an administrator's perspective.

FIGS. 9-54 include a process in an embodiment from a nurse's perspective.

FIGS. 55-74 include a process in an embodiment from a doctor's perspective.

FIGS. 75-95 include a process in an embodiment from a patient's perspective.

FIGS. 99(A), 99(B), and 99(C) include example pseudocode in an embodiment.

FIG. 101 includes example pseudocode in an embodiment.

FIG. 102 includes example pseudocode in an embodiment.

DETAILED DESCRIPTION

Figures 1, 2, 3:
FIGS. 1-3 include a process in an embodiment.

In the following description, numerous specific details are set forth but embodiments of the invention may be practiced without these specific details. Well-known circuits, structures and techniques have not been shown in detail to avoid obscuring an understanding of this description. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner.

An embodiment brings doctors and nurses together on the floor of the hospital so they can visit the patient together. Through location tracking (e.g., WiFi router mapping technology such as the example code found in FIGS. 99(A), (B), (C)) and other software modules the embodiment identifies: (a) nurses on their shift that day, (b) where those nurses are located, and (b) doctors when they arrive on the floor. The embodiment puts the doctors and nurses (and other parties of interest, such as a manager or orderly or assistant) on a digital map overlay of the patient care area. Doctors are asked if they are ready to round and, if so, nurses are then contacted. In response, care team members see one another on the digital hospital map. They can choose to digitally contact each other through a messaging system in the application or simply walk over and find one another on the floor. This sets up a situation where the care team members now physically round with one another and discuss care eye-to-eye with the patient, thereby limiting errors and improving safety and patient and/or care giver satisfaction. An embodiment also has a function for patients to download an application with which the patient can provide feedback outcome data. This data stream may be monitored in real-time, empowering the patient to have a voice in the delivery of the care he or she receives.

An embodiment allows for "room level" location accuracy for users without relying on global positional system (GPS). This allows doctors, nurses, and other members of the care team to be directed to the bedside of patients simultaneously in order to provide the best collaborative care. All of this is done with full HIPAA compliance. More specifically, an embodiment uses WI-FI co-location (see, e.g., FIGS. 99(A), (B), (C)) to promote, facilitate, and verify coordinated healthcare among doctors, nurses, and members of the care team.

An embodiment includes four modules: (1) doctor module, (2) nurse module, (3) administrator module, and (4) patient module.

In an embodiment the doctor module prompts the doctor on his or her arrival to the patient floor. This may be provided using, for example, the code structure of FIGS. 99(A), (B), (C). For instance, the module may communicate "I see you are on 8 West . . . ", "do you want to round with patients", "would you like to see charge nurse on map", and the like. The embodiment may have further options such as displaying: (1) the doctor's patients he has rounded on in the last 24 hours, week, month, and the like, (2) patient's responses to survey questions (e.g., see FIG. 5), (3) "Reports" that present data (e.g., patient satisfaction with medical care or patient's pain levels) (see, e.g., FIGS. 5 and 88), and/or (3) a listing of all patients the doctor needs to "round on"/visit that day. The embodiment may have still other options such as displaying (1) the doctor's performance on his patients over time, (2) the doctor's performance by day, by floor, by nurse attached to him, and/or (3) the doctor's performance over time or by day for each of the rounding categories on a survey. An embodiment may display the doctor's profile (e.g., name, medical specialty as selected from a drop down menu, hospitals covered, and the like). An embodiment may allow messaging whereby a doctor can tap a nurse icon on the map to message her directly. An embodiment passively exits or logs the physician out once Wi-Fi location determines the doctor's mobile phone has exited a particular medical facility floor. An embodiment also, by hovering over a nurse icon on the map, will inform the doctor as to the identity of the nurse.

In an embodiment the nurse module has options such as: (1) nurse signs on and "activates" herself in the system when coming onto a shift, (2) nurses who are activated in the system can see each other's locations on the map, (3) hovering over another nurse's icon will tell the viewer the nurse's identity and tapping nurse's icon will message that nurse directly, (4) the charge nurse has administrative functions on her interface such as, for example, messaging all nurses working under her simultaneously, (5) system prompts a nurse when doctor enters the floor she is working on, (6) system passively exits or logs the nurse out when she or he exits the floor, (7) hovering over the doctor icon on the map will tell nurse who it is. An embodiment allows a nurse to choose patient rooms she is taking care of by tapping the room on the map. This can be updated throughout each shift as patients are admitted and discharged.

In an embodiment the administrator module: (1) focuses on data analysis from doctors and nurses (e.g., data included patient satisfaction survey results), (2) runs reports by physician, nurse, floor, dates of service, patient, groups of patients, and the like, and (3) display maps of any floor and touch/hover over both doctors and nurses and message them if they want.

In an embodiment the patient module: (1) provides a satisfaction survey, (2) prompts a patient to complete the survey each day, (3) reviews generic scores and results on the patient's physicians and nurses, (4) immediately on opening the first time the module obtains personal information from the patient (e.g., name, age, hospital they are admitted to, insurance provider, and the like), and (6) asks the user if the user is the patient or a loved one/surrogate, and the like.

Figures 93, 94, 95:
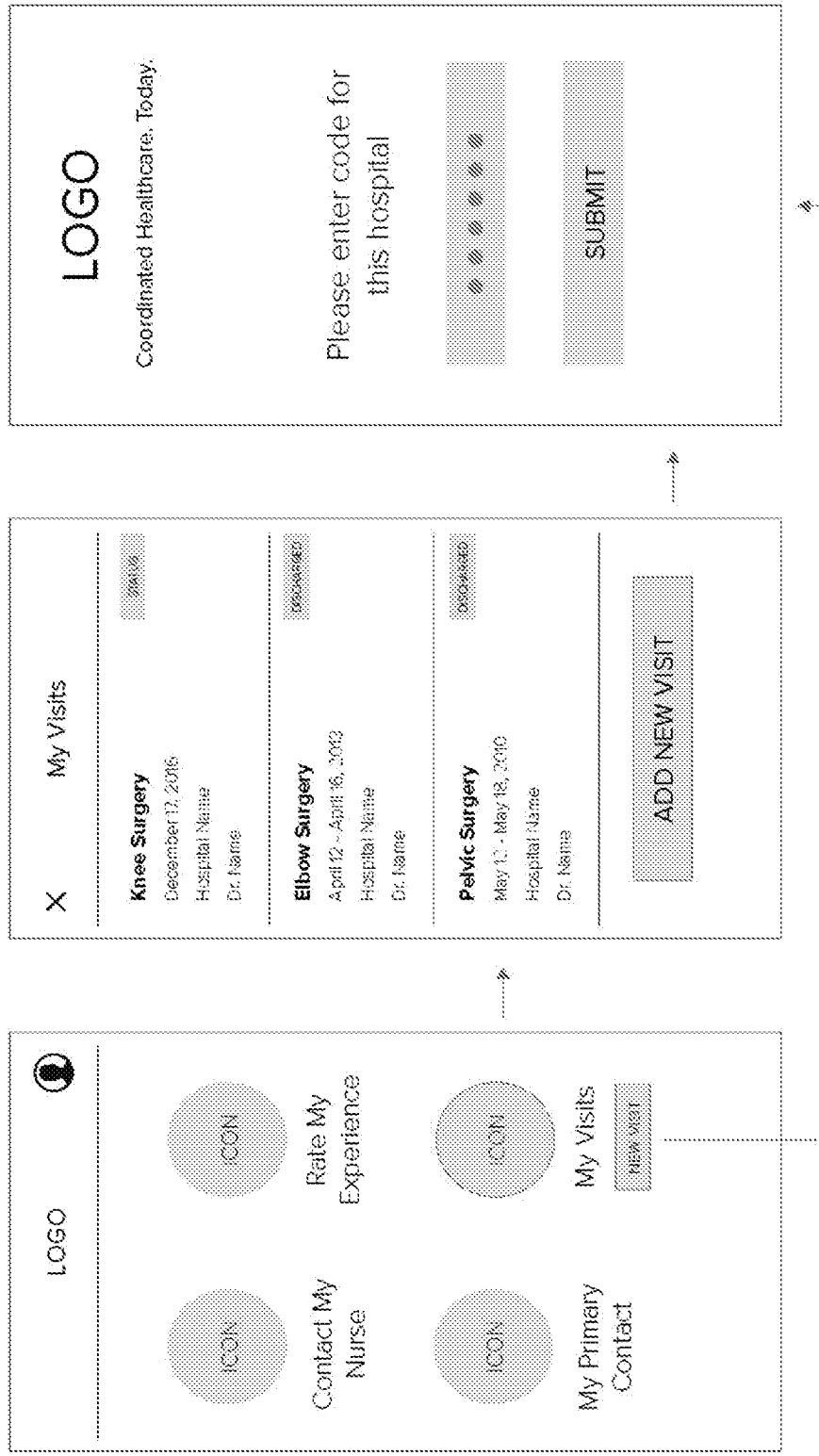

FIGS. 1-95 are now addressed. The figures provide "screen shots" of graphical user interfaces that largely speak for themselves. Regardless, discussion of these figures follows.

FIGS. 1-3 address an Account Creation Screen Flow. FIG. 1: Account creation screen. Email and password needed for login. FIG. 2: User chooses the type of account (e.g., patient, nurse, doctor). FIG. 3: Specific signup code needed to verify account eligibility.

Figure 6:
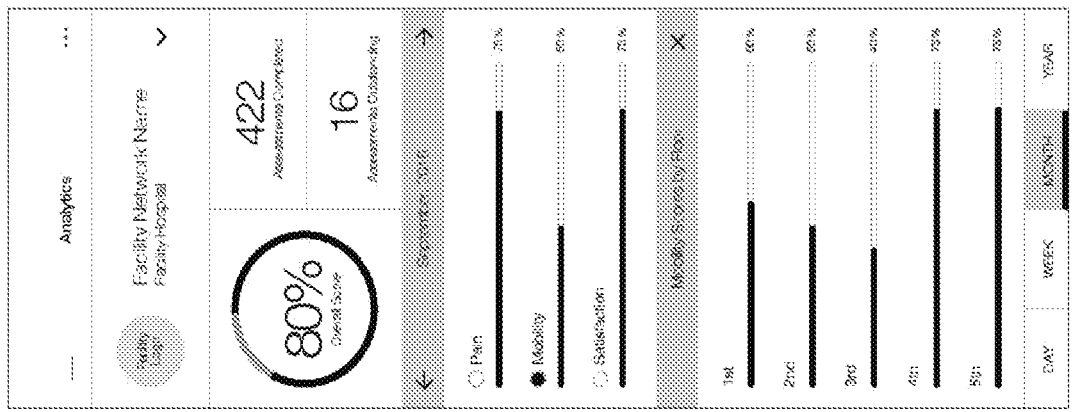
Figure 5:
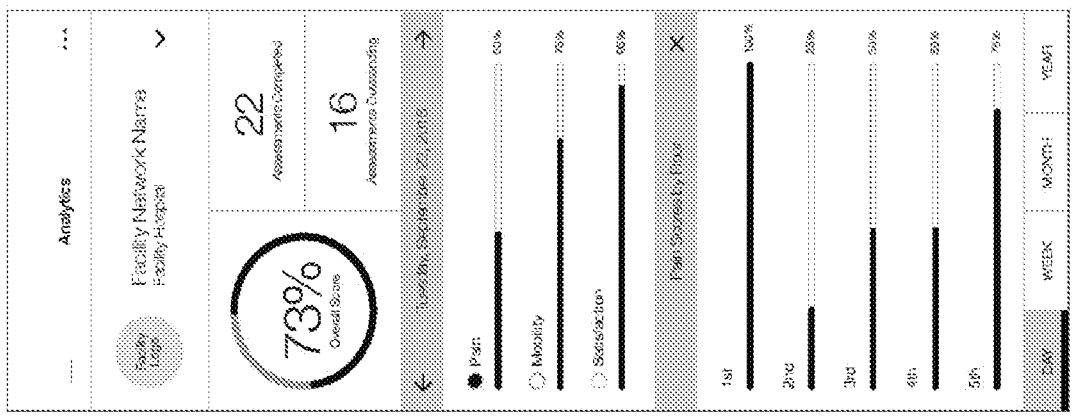
Figure 4:
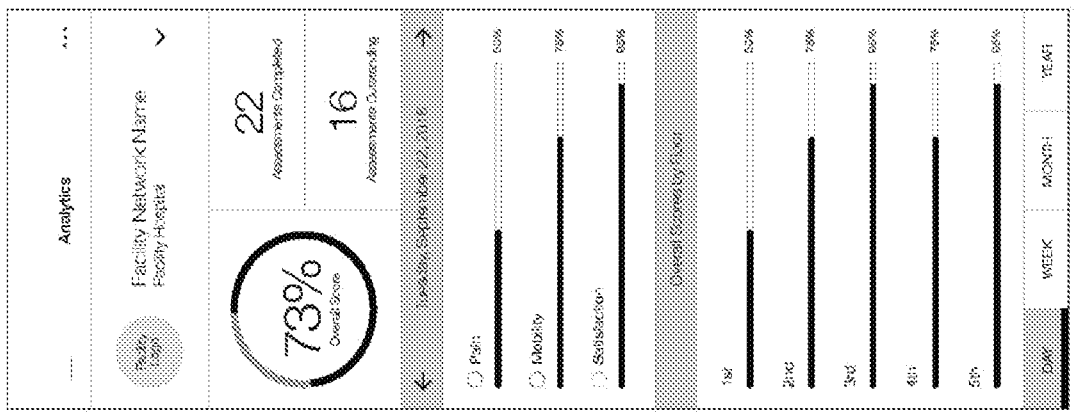
Figures 7, 8, 9:
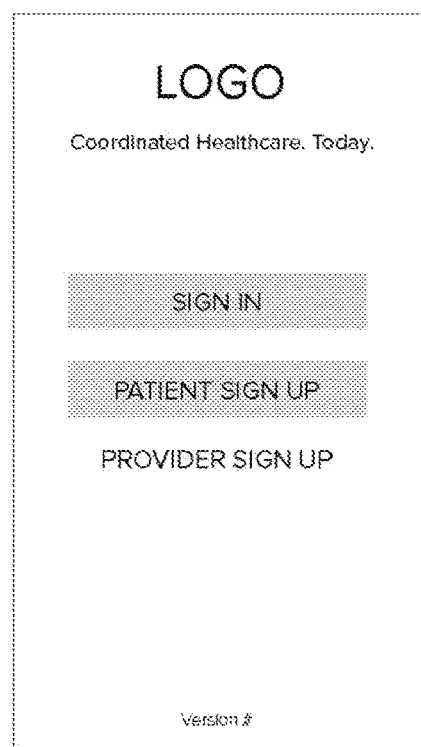

FIGS. 4-8 address an Administrator User Interface Screen Flow. FIGS. 4-6: Administrator screens allow analytic overview of various metrics within patient evaluation tool. These results can be sorted by type (e.g., pain, mobility, satisfaction) and/or by time period (e.g., day, week, month, year). FIGS. 7-8: All evaluations can be seen and sorted according to type and score.

Figures 10, 11:
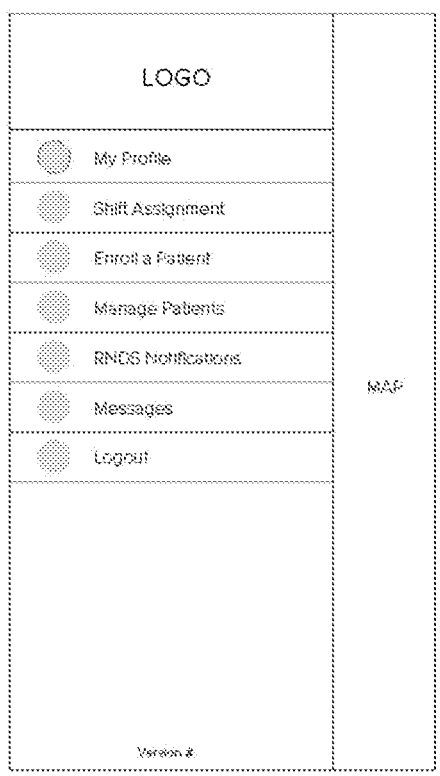
Figures 18, 19, 20:
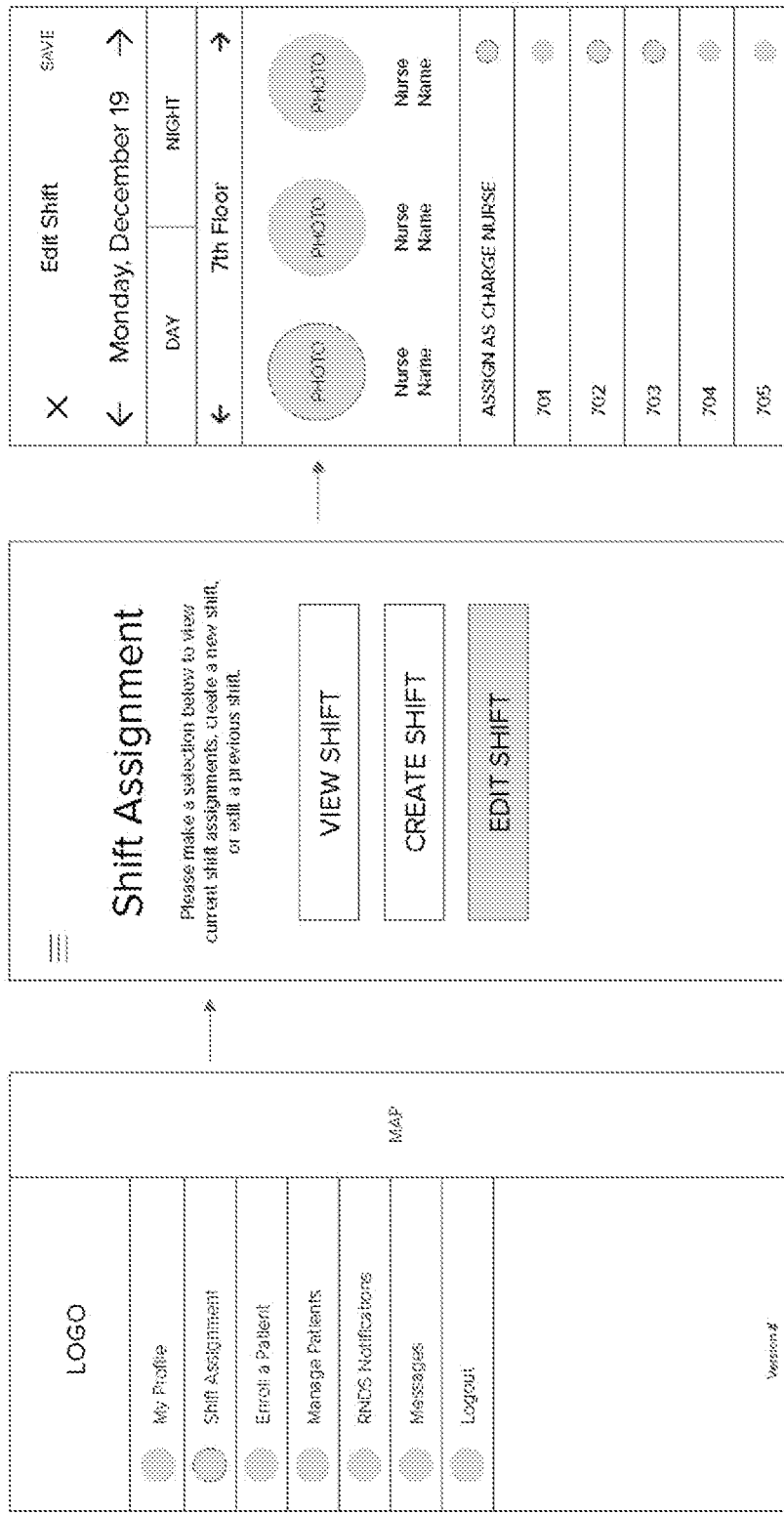
Figures 21, 22:
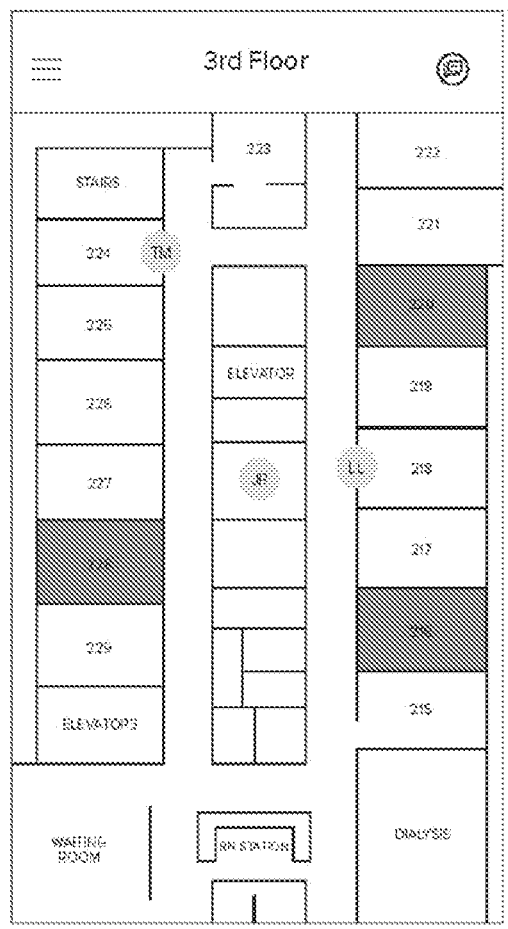
Figure 25:
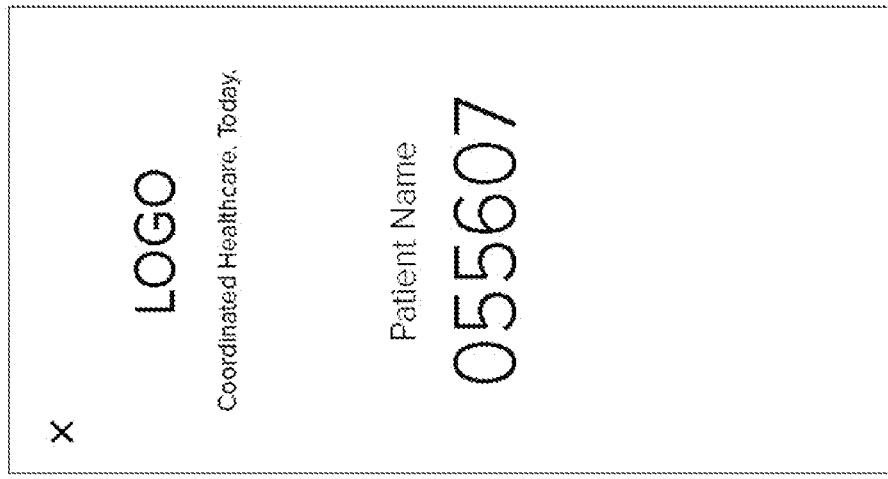
Figure 24:
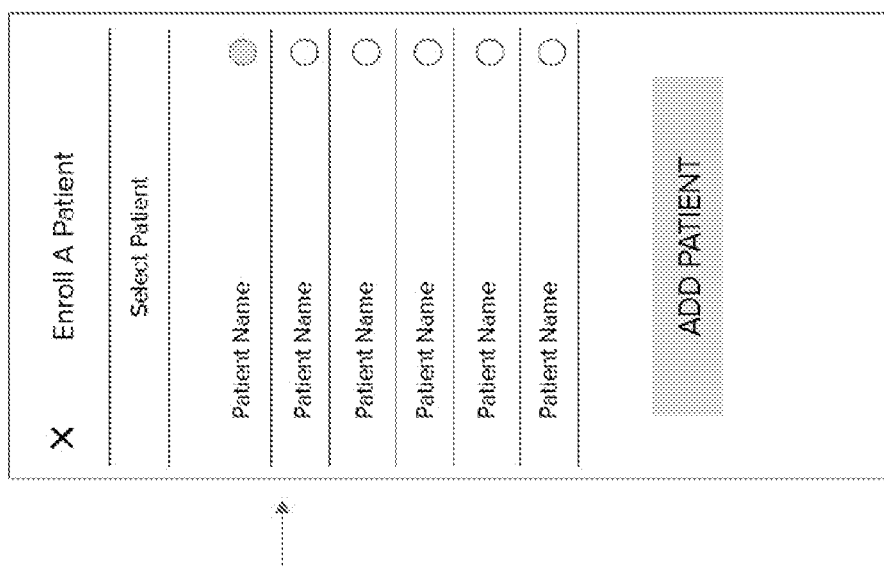
Figure 23:
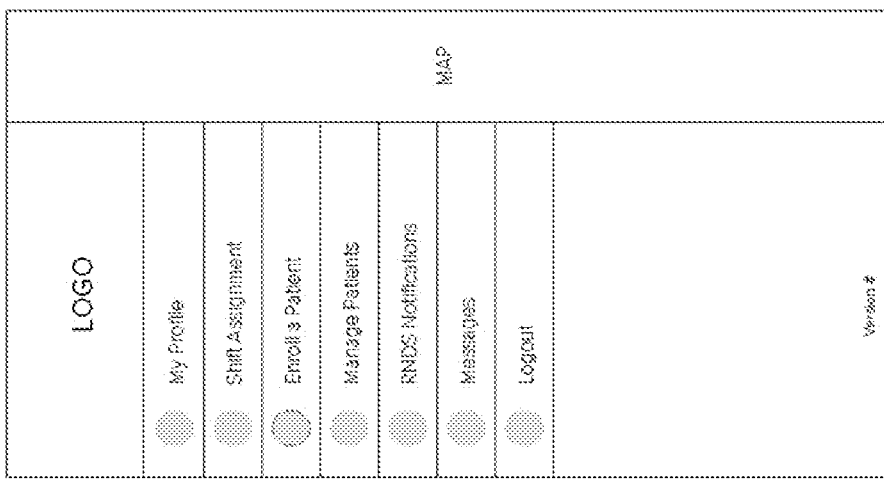
Figure 28:
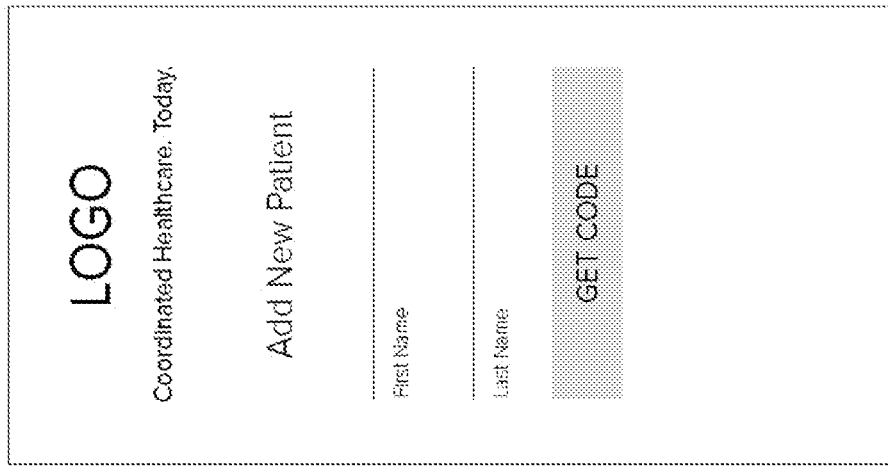
Figure 27:
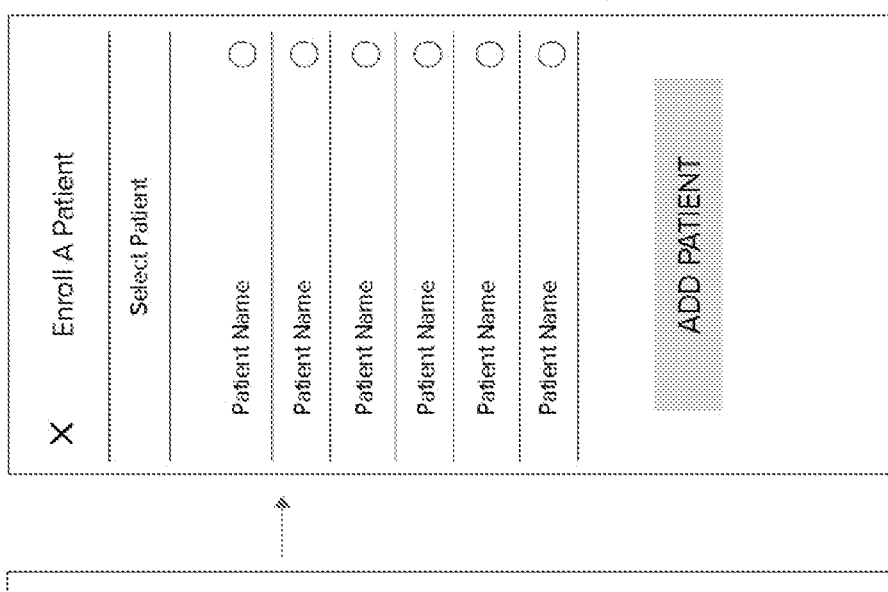
Figure 26:
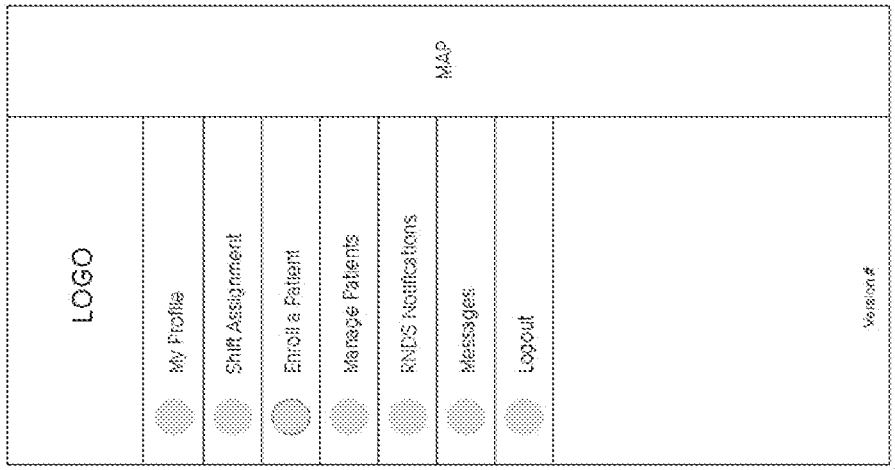
Figures 29, 30, 31, 32:
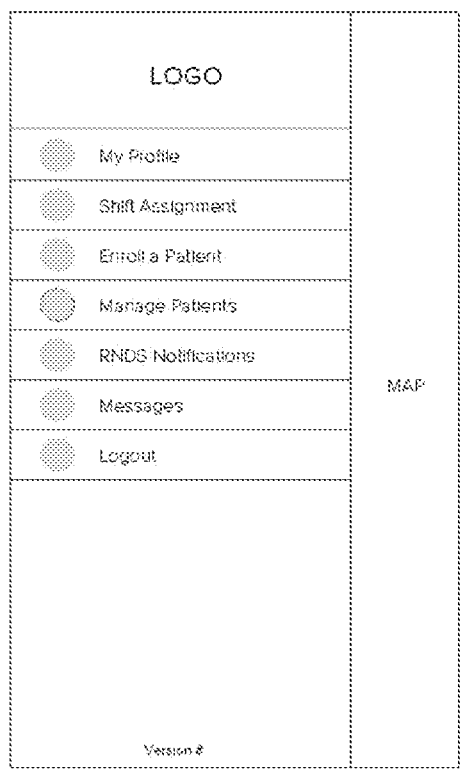
Figure 53:
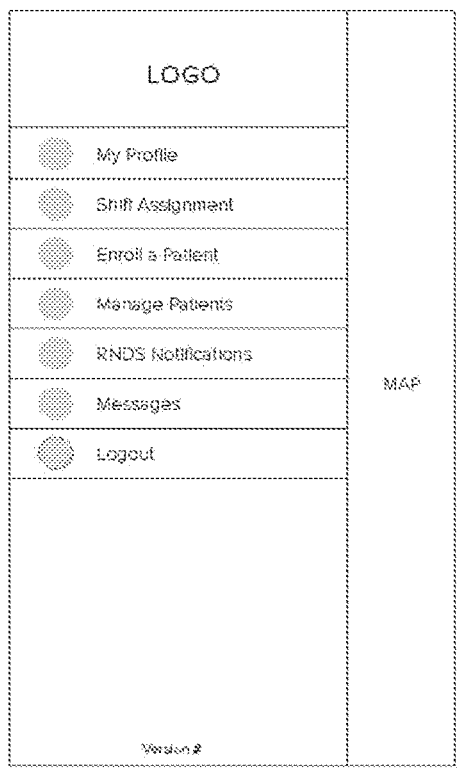
Figure 54:
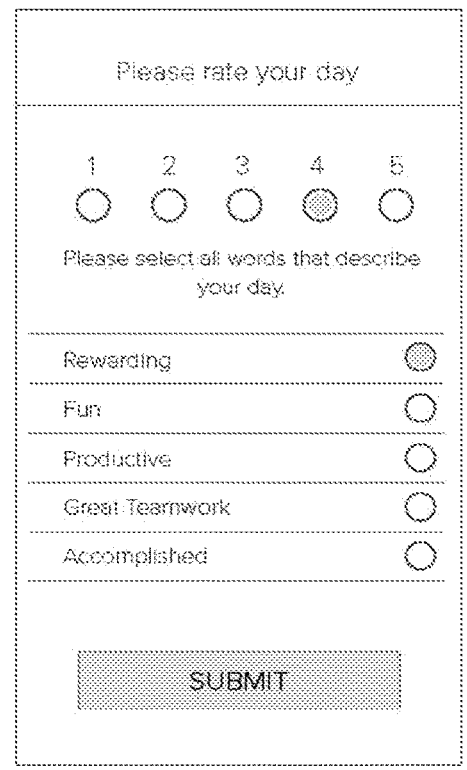

FIGS. 9-54 address a Nurse User Interface Screen Flow. FIG. 9: User login screen. FIGS. 10-11: Side menu with nurse user functionality options. "My profile" identifies the user and can be edited to indicate user preferences. FIGS. 12-14: Under "Shift Assignment", "View Shift" allows the user to see a list of all staff assignments that have been entered for a specific unit. This can be sorted by date to view current assignments or assignments for other dates. FIGS. 15-17: Under "Shift Assignment", "Create Shift" page allows shift assignments to be manually entered by clicking on nurse name and then selecting rooms and rolls for the indicated shift. FIGS. 18-20: Under "Shift Assignment", "Edit Shift" allows changes to be made in the shift to indicated changing assignments throughout a shift. FIG. 21: The interactive map view is the user home page. Within the map page specific rooms can be clicked and highlighted, or location pins with staff initials can be clicked. FIG. 22: By clicking on a room, the user profile of the staff assigned to that room will be displayed. Also, by clicking on a location pin in the map view of FIG. 21, the user profile (FIG. 22) will be displayed along with current assignments. Message and phone icons (but other embodiments may include other means of communication) are present to allow direct communication with the caregiver. FIGS. 23-25: Under "Enroll Patient", a patient can be selected from a pre-populated list in order to generate a unique user code for the patient to download the application (see FIGS. 87-95 for patient perspective flows). FIGS. 26-28: Under "Enroll Patient", the nurse has the ability to manually add a new patient and generate a unique code for the patient to download the app. FIGS. 29-32: Under "Manage Patient", "Change Patient Status" allows a user to select a specific patient in the unit and indicate a move of the patient to a different room or discharge. A notification of the change of status is then automatically sent to the patient's designated primary caregiver. FIGS. 33-36: Under "Manage Patient", "Message Patient" allows the caregiver to send a secure message (e.g., a HIPPA encrypted message) to the selected patient. FIGS. 37-45: Under "Manage Patient", "Alert Family" allows the caregiver to choose from a list of pre-populated notifications/communication content or create a custom message to send to a designated member of the patient's family. The pre-populated message choices are customizable in different care facility environments. FIGS. 46-49: Under "RNDS Notifications", the caregiver can see and respond to a list of notifications from other users, such as doctors. These notifications are sent by doctors to nurses and other caregivers indicating a desire for the caregiver to round on a patient with them. (See FIGS. 61-62 for a description of the RNDS request that is sent by the doctor). FIGS. 50-52: Under "Messages", a list of message threads is kept with the ability to reply or create HIPPA secure messages that can be sent to other caregivers. FIGS. 53-54: Under "Logout", the user is given the option to logout of the application. By logging out of the application, a brief survey of the shift is given. The user is able to give a rating of their day and choose a word that best describes the reason for the rating. Keeping metrics, whether they are on a nurse's view of his or her shift or on a patient's experience of pain, helps health care provider teams address problem situations more readily to help improve health care.

Figure 55:
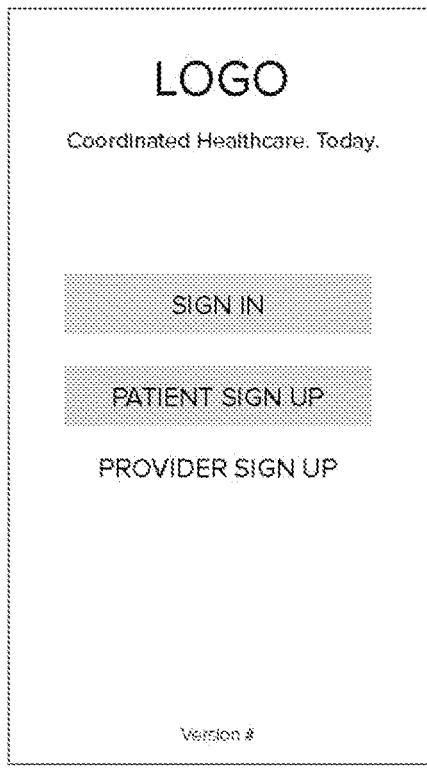
Figure 56:
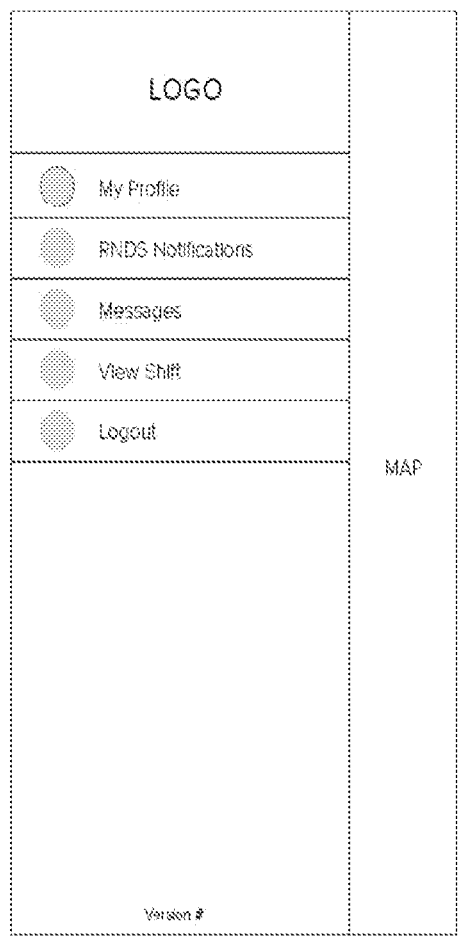
Figure 57:
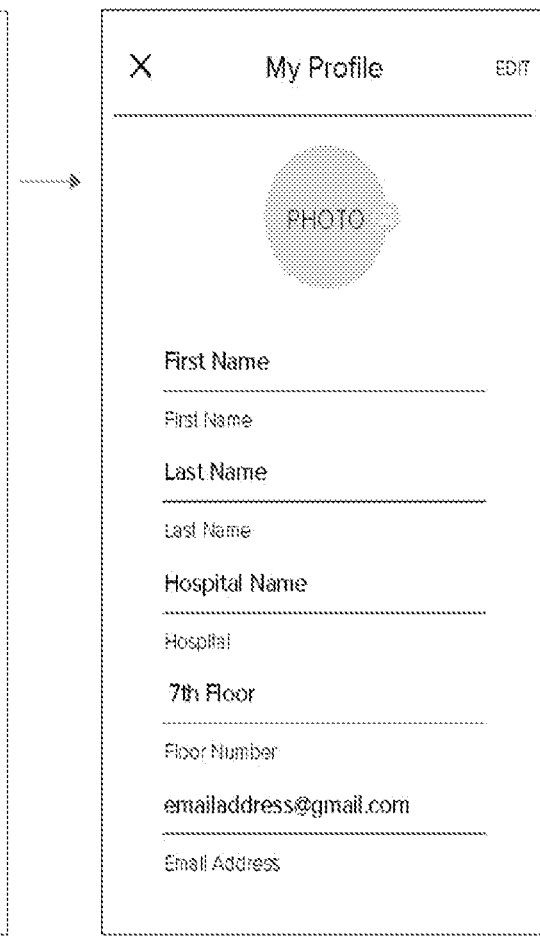
Figure 67:
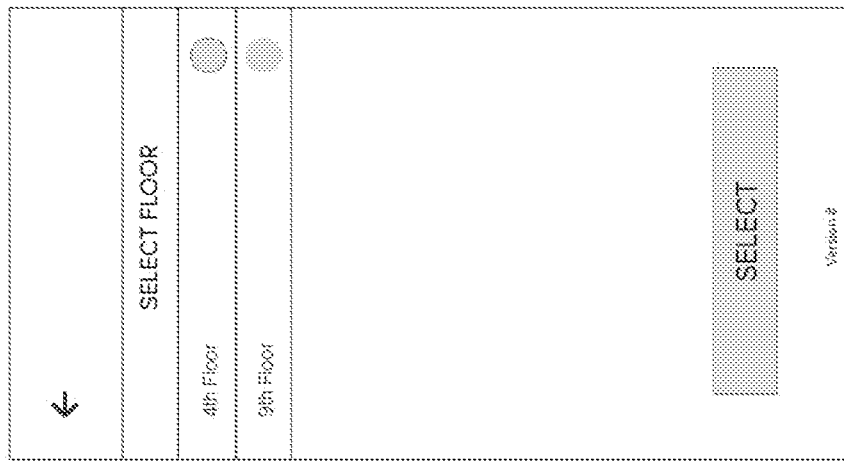
Figure 66:
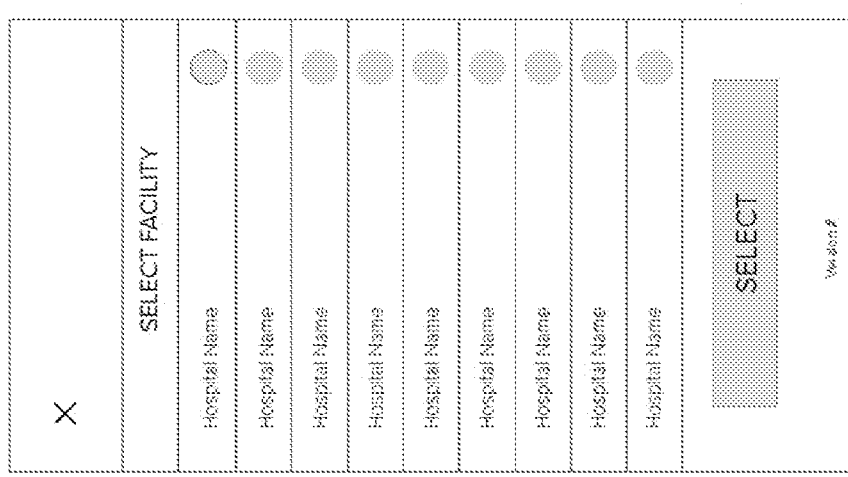
Figure 65:
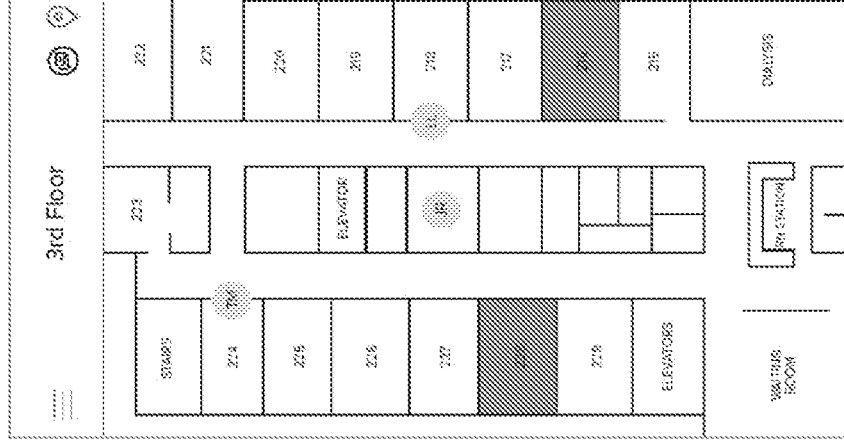
Figures 68, 69:
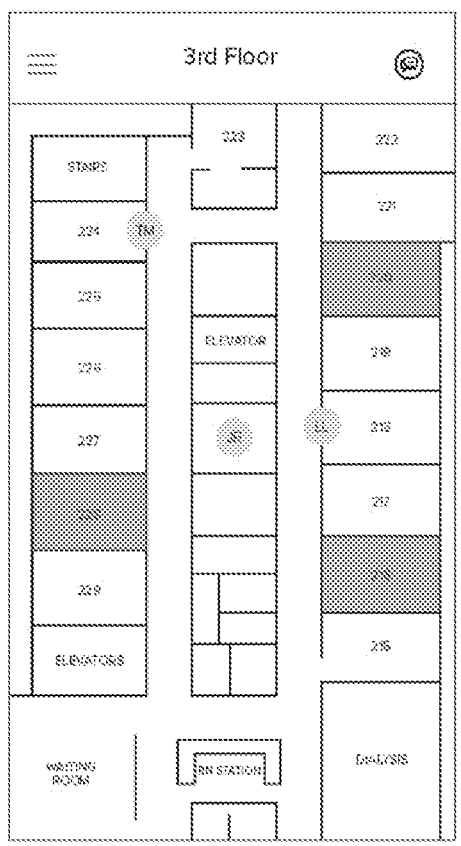
Figures 70, 71, 72:
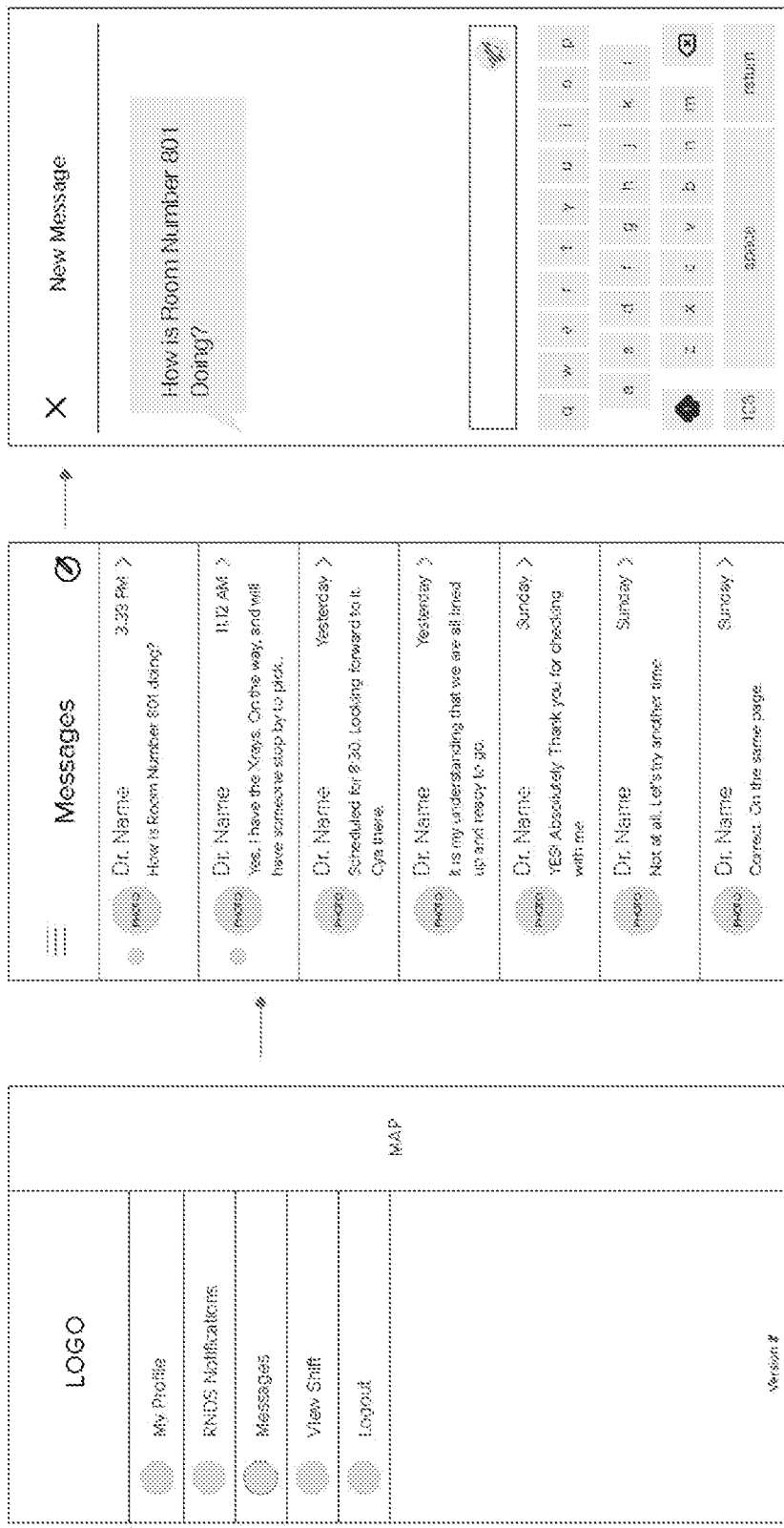
Figure 73:
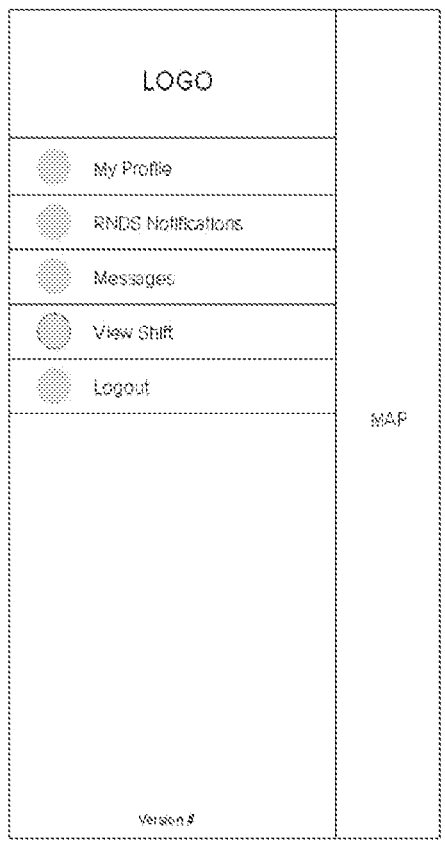
Figure 74:
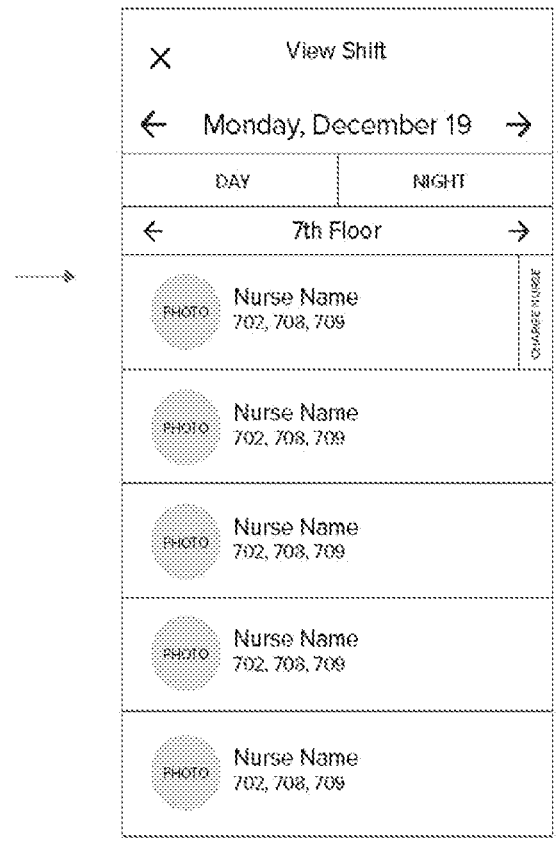

FIGS. 55-74 address a Doctor User Interface Screen Flow. FIG. 55: This is the same screen as FIG. 9 and is the common login screen for all user types. FIGS. 56-57: Side menu with doctor user functionality options. "My profile" identifies the user and can be edited to indicate user preferences. FIGS. 58-60: The initial welcome screen allows the doctor to choose the facility and the unit/floor that will appear on the map. FIGS. 61-62: The interactive map view of the chosen unit is the doctor home page. Within the map page, specific rooms can be clicked and highlighted and/or location pins with staff initials can be clicked. When a specific nurse or caregiver is chosen (whether by first selecting a room to which the nurse is assigned or by selecting the nurse icon on the map), the doctor has the ability to send a "rnds request" (a request to round with the doctor) to the caregiver. FIGS. 63-64: Under "Rnds Notifications", the user is given a list of rounds requests that have been sent and replies received. See FIGS. 46-49 for further description. FIGS. 65-67: In the top right hand corner of the map page is a location icon (shown in FIG. 65) that allows the user to change facilities or floors to view a different location. FIGS. 68-69: Within the map page, specific rooms can be clicked and highlighted, or location pins with staff initials can be clicked. When a specific nurse or caregiver is chosen, the doctor has the ability to send a rounds request to the caregiver, or click "show location" to give an updated location of the chosen caregiver (although real time location information is provided in other embodiments as addressed in FIGS. 99(A), (B), (C)). The user is then able to click on the message icon or the call icon to communicate directly with the caregiver for a chosen room. FIGS. 70-72: Under "Messages", a list of message threads is kept with the ability to reply or create HIPPA secure messages that can be sent to other caregivers. FIGS. 73-74: Under "View Shift", the user sees a list of staff assignments that have been entered for a specific unit. This can be sorted by date to view current assignments or assignments for other dates.

Figures 81, 82, 83:
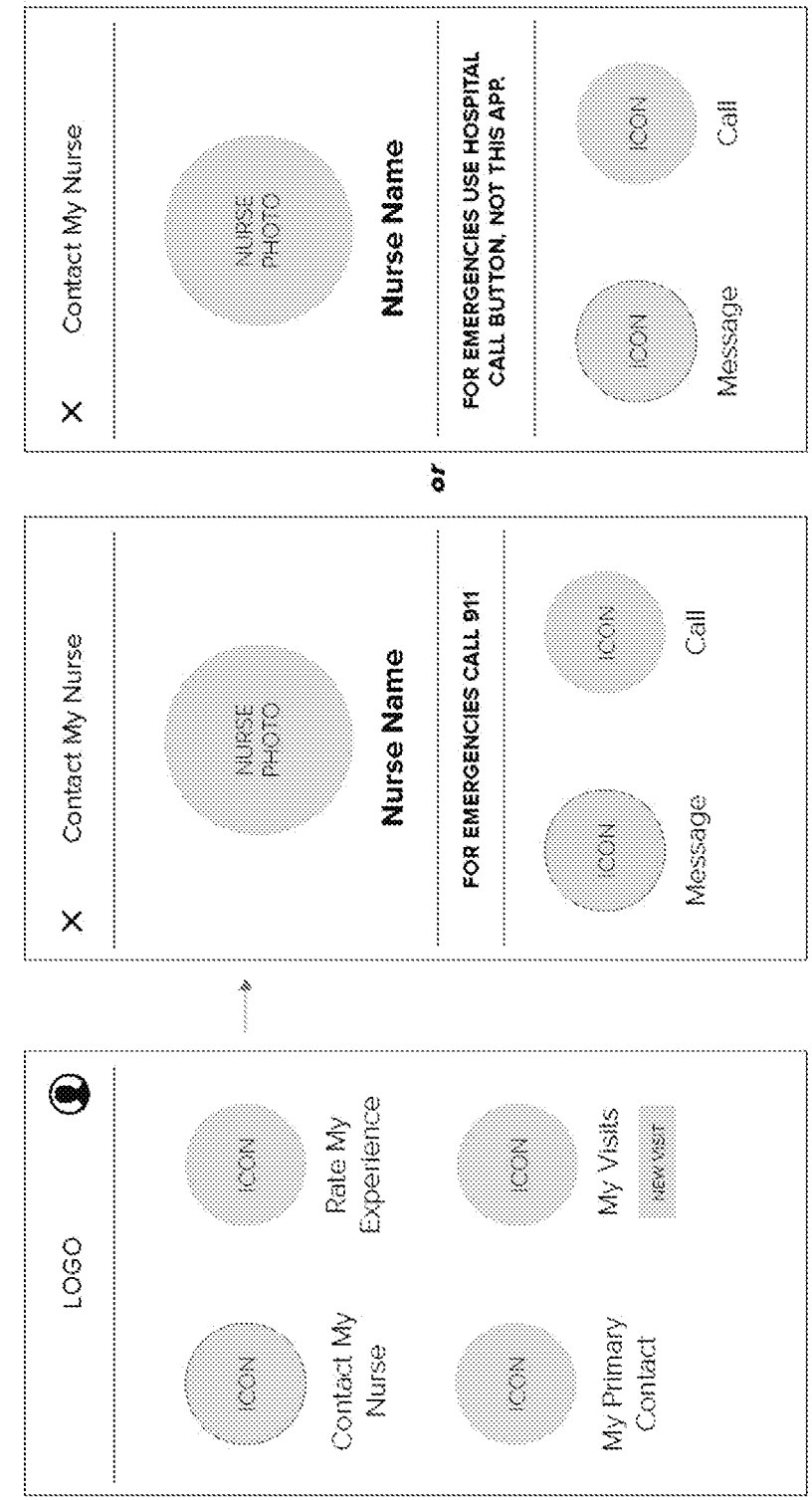
Figures 87, 88:
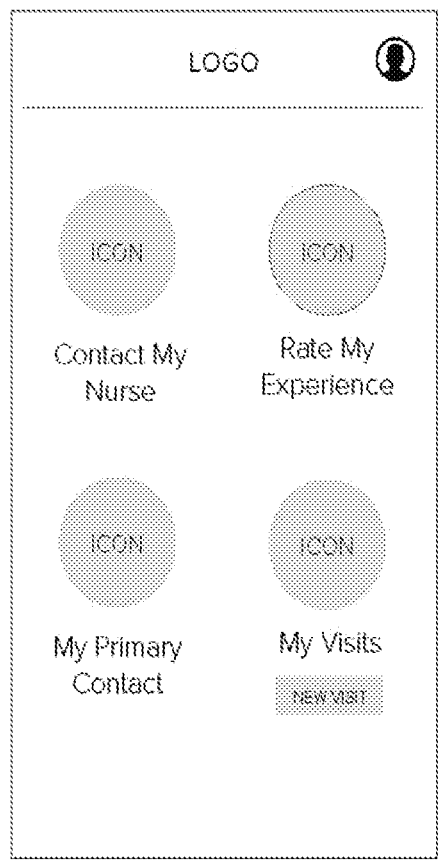

FIGS. 75-95 address a Patient User Interface Screen Flow. FIGS. 75-80: The initial patient landing gives the patient the ability to login to the application or create their user profile for the application. In order to create a user profile the patient must have a unique signup code (in an embodiment) provided to them by the facility (FIGS. 23-28 describe the creation of this code by the facility or the nurse). The patient can then create email and password login information, accept the terms and conditions, and complete their profile. FIG. 81: This is the patient interface homepage. FIGS. 82-86: By clicking the "contact my nurse button", the patient is able to see a photo and first name of the nurse and either send a HIPPA secure message or call the nurse. FIGS. 87-88: By clicking the "rate my experience" button, the patient is able to complete a patient satisfaction inventory. This questionnaire generates real-time data that can be used to create analytics for the designated administrators or other users (see FIGS. 4-8). The questions contained in this inventory are customizable by the individual facility. FIGS. 89-92: By clicking the "My Primary Contact" button, the patient is able to enter the name and phone number they want to be notified by the hospital when there are status changes or specific care information needed to be shared with a family member. (See FIGS. 37-45 for a description of the notification process). FIGS. 93-95: By clicking the "My Visits" button, the patient can see a list of current or previous hospital stays or create a new visit by clicking the "new visit" button and adding the unique hospital code for that visit.

Figure 96:
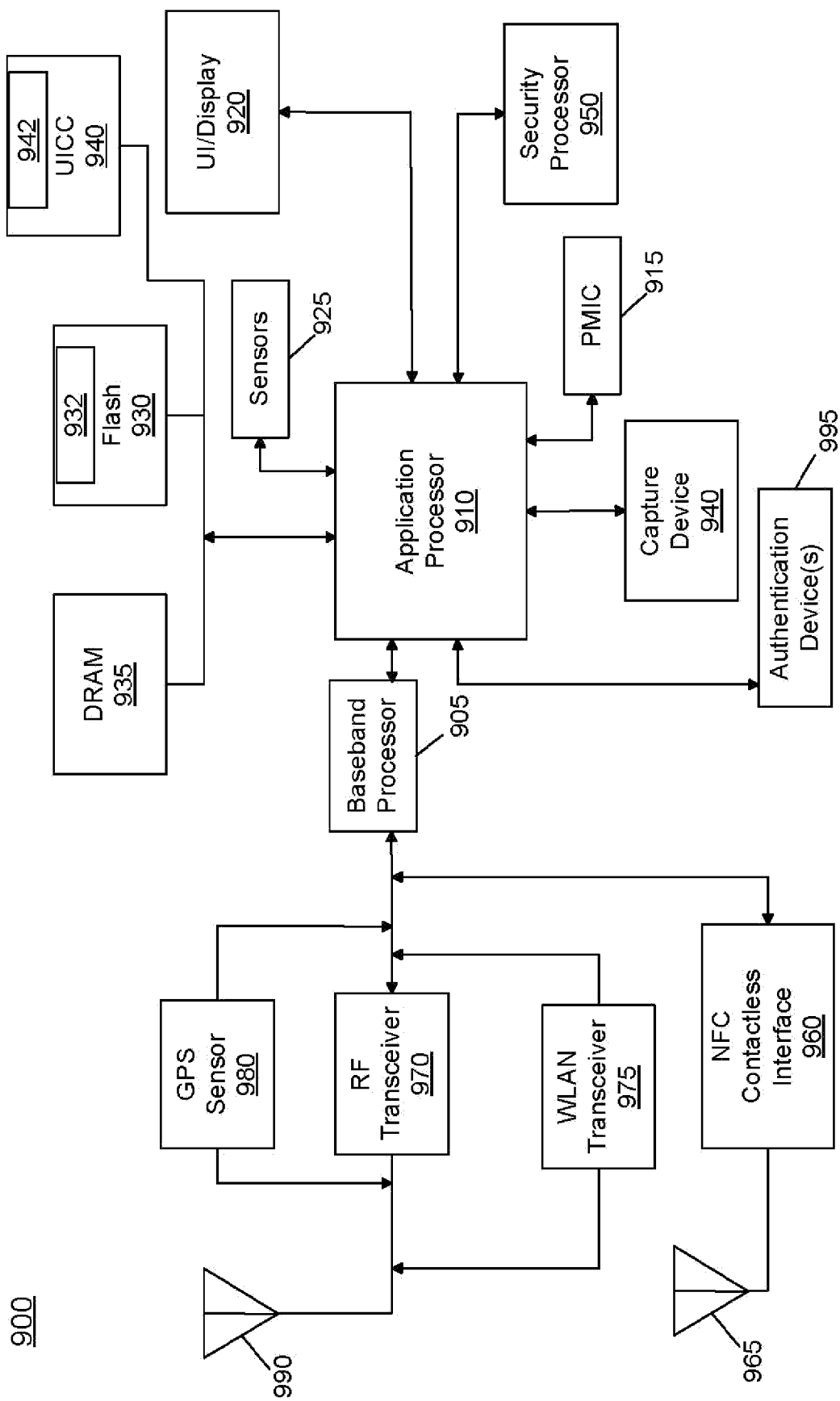
FIGS. 96-98 include systems for use with embodiments.
Figure 97:
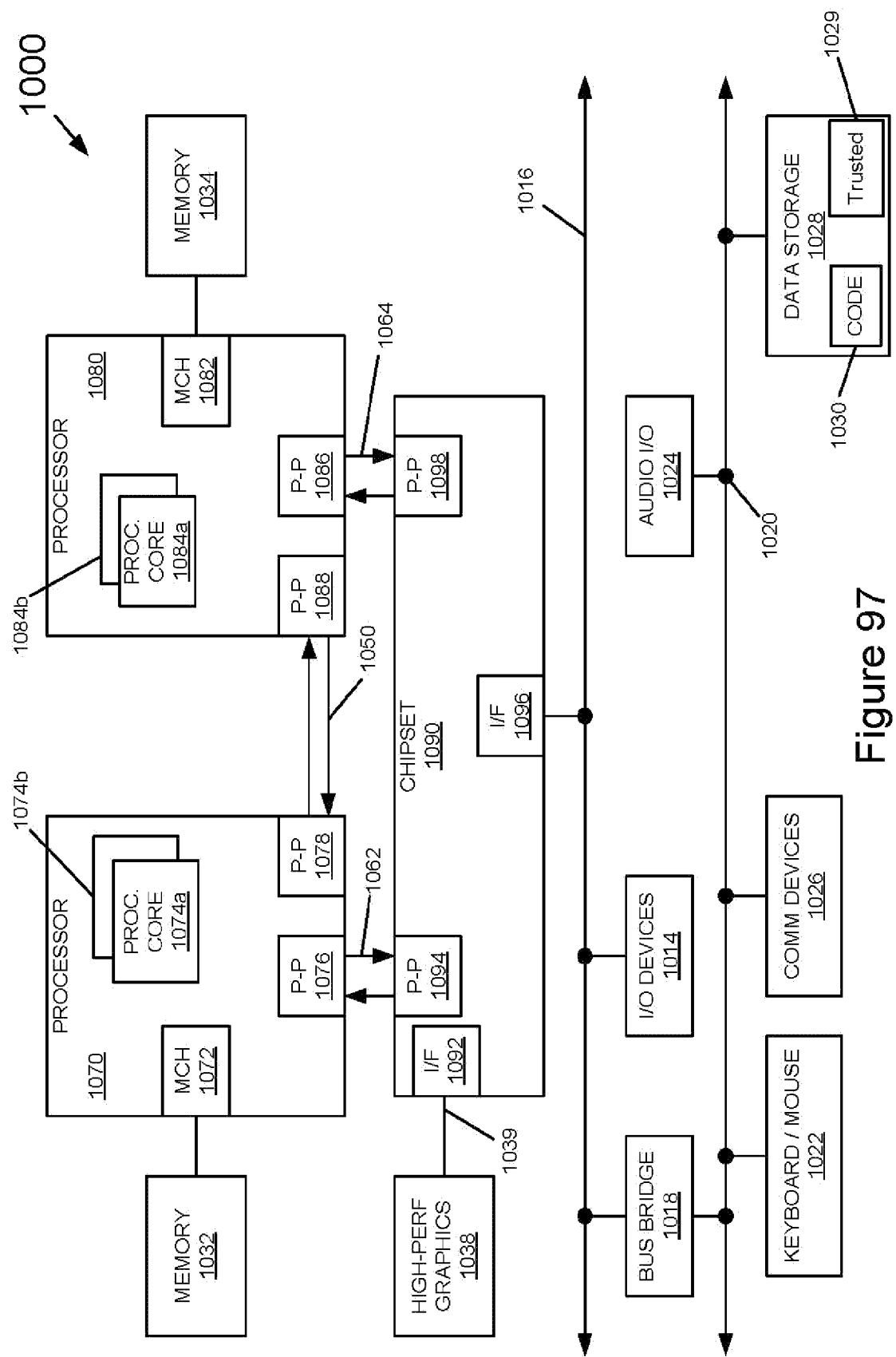
Figure 98:
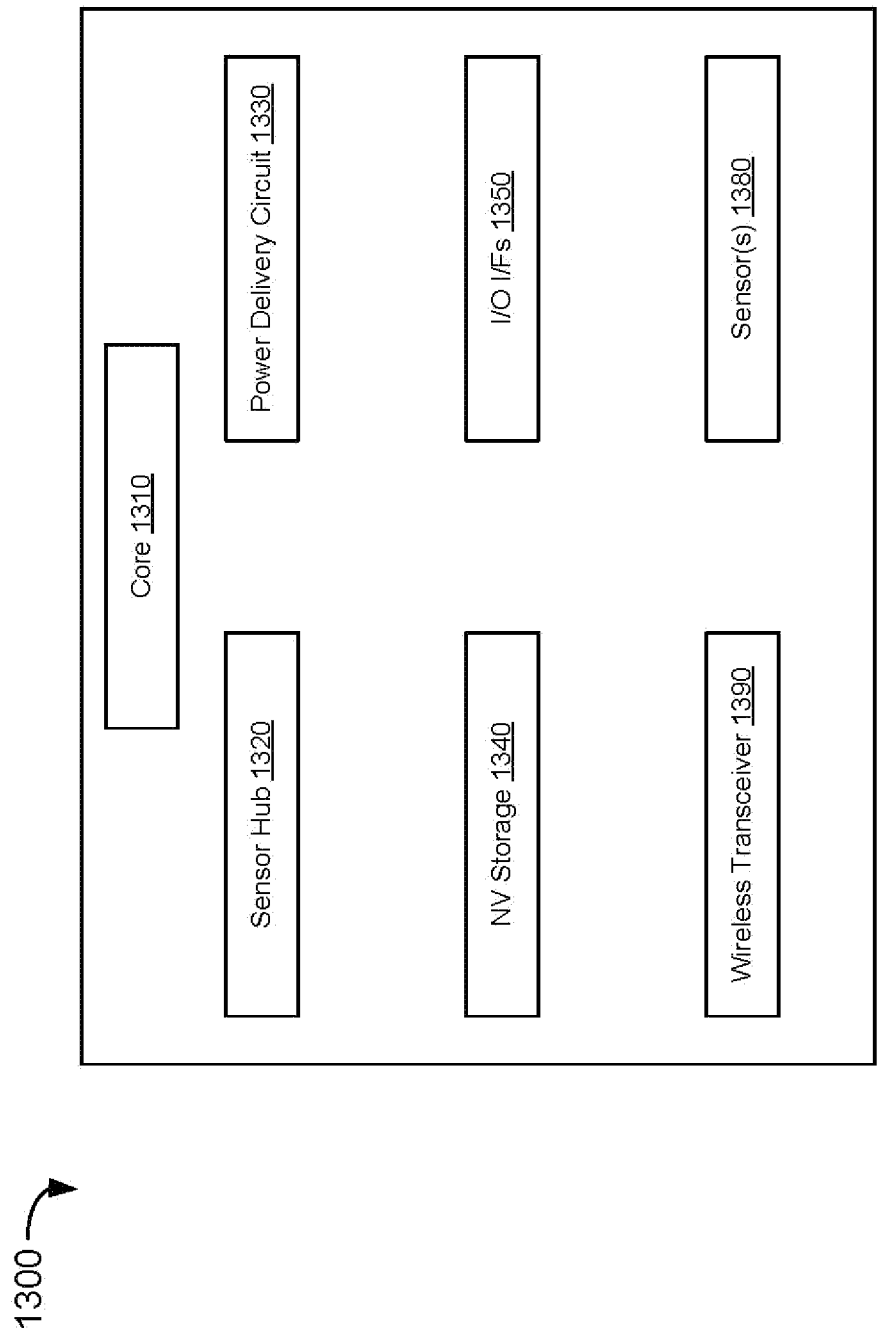

Embodiments may be implemented using the systems shown in FIGS. 96-98.

Referring now to FIG. 96, shown is a block diagram of an example system with which embodiments can be used. As seen, system 900 may be a smartphone or other wireless communicator or any other internet of things (IoT) device. A baseband processor 905 is configured to perform various signal processing with regard to communication signals to be transmitted from or received by the system. In turn, baseband processor 905 is coupled to an application processor 910, which may be a main CPU of the system to execute an OS and other system software, in addition to user applications such as many well-known social media and multimedia apps. Application processor 910 may further be configured to perform a variety of other computing operations for the device. In turn, application processor 910 can couple to a user interface/display 920 (e.g., touch screen display). In addition, application processor 910 may couple to a memory system including a non-volatile memory, namely a flash memory 930 and a system memory, namely a DRAM 935. In some embodiments, flash memory 930 may include a secure portion 932 in which secrets and other sensitive information may be stored. As further seen, application processor 910 also couples to a capture device 945 such as one or more image capture devices that can record video and/or still images. A universal integrated circuit card (UICC) 940 comprises a subscriber identity module, which in some embodiments includes a secure storage 942 to store secure user information. System 900 may further include a security processor 950 (e.g., Trusted Platform Module (TPM)) that may couple to application processor 910. A plurality of sensors 925, including one or more multi-axis accelerometers may couple to application processor 910 to enable input of a variety of sensed information such as motion and other environmental information. In addition, one or more authentication devices 995 may be used to receive, for example user biometric input for use in authentication operations. As further illustrated, a near field communication (NFC) contactless interface 960 is provided that communicates in a NFC near field via an NFC antenna 965. While separate antennae are shown, understand that in some implementations one antenna or a different set of antennae may be provided to enable various wireless functionalities. A power management integrated circuit (PMIC) 915 couples to application processor 910 to perform platform level power management. To this end, PMIC 915 may issue power management requests to application processor 910 to enter certain low power states as desired. Furthermore, based on platform constraints, PMIC 915 may also control the power level of other components of system 900. To enable communications to be transmitted and received such as in one or more IoT networks, various circuitry may be coupled between baseband processor 905 and an antenna 990. Specifically, a radio frequency (RF) transceiver 970 and a wireless local area network (WLAN) transceiver 975 may be present. In general, RF transceiver 970 may be used to receive and transmit wireless data and calls according to a given wireless communication protocol such as 3G or 4G wireless communication protocol such as in accordance with a code division multiple access (CDMA), global system for mobile communication (GSM), long term evolution (LTE) or other protocol. In addition a GPS sensor 980 may be present, with location information being provided to security processor 950 for use as described herein when context information is to be used in a pairing process. Other wireless communications such as receipt or transmission of radio signals (e.g., AM/FM) and other signals may also be provided. In addition, via WLAN transceiver 975, local wireless communications, such as according to a Bluetooth™ or IEEE 802.11 standard can also be realized.

Referring now to FIG. 97, shown is a block diagram of a system in accordance with another embodiment of the present invention. Multiprocessor system 1000 is a point-to-point interconnect system such as a server system, and includes a first processor 1070 and a second processor 1080 coupled via a point-to-point interconnect 1050. Each of processors 1070 and 1080 may be multicore processors such as SoCs, including first and second processor cores (i.e., processor cores 1074*a* and 1074*b* and processor cores 1084*a* and 1084*b*), although potentially many more cores may be present in the processors. In addition, processors 1070 and 1080 each may include a secure engine 1075 and 1085 to perform security operations such as attestations, IoT network onboarding or so forth. First processor 1070 further includes a memory controller hub (MCH) 1072 and point-to-point (P-P) interfaces 1076 and 1078. Similarly, second processor 1080 includes a MCH 1082 and P-P interfaces 1086 and 1088. MCH's 1072 and 1082 couple the processors to respective memories, namely a memory 1032 and a memory 1034, which may be portions of main memory (e.g., a DRAM) locally attached to the respective processors. First processor 1070 and second processor 1080 may be coupled to a chipset 1090 via P-P interconnects 1052 and 1054, respectively. Chipset 1090 includes P-P interfaces 1094 and 1098.

Furthermore, chipset 1090 includes an interface 1092 to couple chipset 1090 with a high performance graphics engine 1038, by a P-P interconnect 1039. In turn, chipset 1090 may be coupled to a first bus 1016 via an interface 1096. Various input/output (I/O) devices 1014 may be coupled to first bus 1016, along with a bus bridge 1018 which couples first bus 1016 to a second bus 1020. Various devices may be coupled to second bus 1020 including, for example, a keyboard/mouse 1022, communication devices 1026 and a data storage unit 1028 such as a non-volatile storage or other mass storage device. As seen, data storage unit 1028 may include code 1030, in one embodiment. As further seen, data storage unit 1028 also includes a trusted storage 1029 to store sensitive information to be protected. Further, an audio I/O 1024 may be coupled to second bus 1020.

Embodiments may be used in environments where IoT devices may include wearable devices or other small form factor IoT devices. Referring now to FIG. 98, shown is a block diagram of a wearable module 1300 in accordance with another embodiment. In one particular implementation, module 1300 may be an Intel® Curie™ module that includes multiple components adapted within a single small module that can be implemented as all or part of a wearable device. As seen, module 1300 includes a core 1310 (of course in other embodiments more than one core may be present). Such core may be a relatively low complexity in-order core, such as based on an Intel Architecture® Quark™ design. In some embodiments, core 1310 may implement a TEE as described herein. Core 1310 couples to various components including a sensor hub 1320, which may be configured to interact with a plurality of sensors 1380, such as one or more biometric, motion environmental or other sensors. A power delivery circuit 1330 is present, along with a non-volatile storage 1340. In an embodiment, this circuit may include a rechargeable battery and a recharging circuit, which may in one embodiment receive charging power wirelessly. One or more input/output (TO) interfaces 1350, such as one or more interfaces compatible with one or more of USB/SPI/I2C/GPIO protocols, may be present. In addition, a wireless transceiver 1390, which may be a Bluetooth™ low energy or other short-range wireless transceiver is present to enable wireless communications as described herein. Understand that in different implementations a wearable module can take many other forms. Wearable and/or IoT devices have, in comparison with a typical general purpose CPU or a GPU, a small form factor, low power requirements, limited instruction sets, relatively slow computation throughput, or any of the above.

Embodiments may be used in many different types of systems. For example, in one embodiment a communication device can be arranged to perform the various methods and techniques described herein. Of course, the scope of the present invention is not limited to a communication device, and instead other embodiments can be directed to other types of apparatus for processing instructions, or one or more machine readable media including instructions that in response to being executed on a computing device, cause the device to carry out one or more of the methods and techniques described herein.

Embodiments may be implemented in code and may be stored on a non-transitory storage medium having stored thereon instructions which can be used to program a system to perform the instructions. Embodiments also may be implemented in data and may be stored on a non-transitory storage medium, which if used by at least one machine, causes the at least one machine to fabricate at least one integrated circuit to perform one or more operations. The storage medium may include, but is not limited to, any type of disk including floppy disks, optical disks, solid state drives (SSDs), compact disk read-only memories (CD-ROMs), compact disk rewritables (CD-RWs), and magneto-optical disks, semiconductor devices such as read-only memories (ROMs), random access memories (RAMs) such as dynamic random access memories (DRAMs), static random access memories (SRAMs), erasable programmable read-only memories (EPROMs), flash memories, electrically erasable programmable read-only memories (EEPROMs), magnetic or optical cards, or any other type of media suitable for storing electronic instructions.

Various examples are now addressed.

Example 1

A method executed by at least one processor comprising: displaying to a first physician, via a display coupled to the at least one processor and at least one memory, at least one of: (a)(i) a map of a hospital floor, (a)(ii) a first patient identifier, and (a)(iii) a second patient identifier, wherein (b)(i) the map simultaneously displays first and second rooms of the hospital floor, (b)(ii) a first patient is assigned to the first room and the first patient identifier and a second patient is assigned to the second room and a second identifier, and (b)(iii) a first nurse is assigned to the first room and the first patient identifier and a second nurse is assigned to the second room and the second identifier; receiving a first selection from the first physician and via the display, the first selection comprising at least one of the displayed first room and the displayed first patient identifier; displaying a first profile of the first nurse in response to receiving the first selection; receiving a second selection, the second selection comprising a communication method from the first physician in response to displaying the first profile of the first nurse; and sending a communication from the first physician to the first nurse in response to receiving the second selection.

See, for example, FIG. 101 for a related embodiment.

For instance, a doctor may be determined to be within range of a WiFi hub. Upon such recognition the doctor may be prompted regarding whether he or she wants to engage with the rounding software product. The doctor may choose to engage and then be shown a map of rooms (e.g., FIG. 61) in a section of a building. Possibly a certain number of the rooms are color coded or highlighted indicating those rooms have patients he needs to visit. However, the doctor may instead be shown a list of patient identifiers (e.g., FIG. 38) such as patient names, patient rooms (that indirectly identify the patient), patient codes (that indirectly identify the patient). The doctor may then select a room or a patient identifier to quickly determine which staff member is assigned (presently at that very moment) to room and/or patient (e.g., FIG. 62). The doctor receives this information with very little effort considering most of the work is done automatically once the doctor is within a predefined range of a WiFi node. The doctor may then choose a communication method such as a phone call or SMS message (e.g., FIG. 62) to communicate with a care giver that is assigned to the room/patient of interest.

The assignments between, for example, a nurse to a room or patient may be done using a look-up table or other such software architecture.

Another version of example 1 includes Example 1. A method executed by at least one processor comprising: displaying to a first physician, via a display coupled to the at least one processor and at least one memory, a map of a hospital floor, wherein (a)(i) the map simultaneously displays first and second rooms of the hospital floor, (a)(ii) a first patient is assigned to the first room and a second patient is assigned to the second room, and (b)(iii) a first nurse is assigned to the first room; receiving a first selection from the first physician and via the display, the first selection comprising the displayed first room; displaying a first profile of the first nurse in response to receiving the first selection; receiving a second selection, the second selection comprising a communication method from the first physician in response to displaying the first profile of the first nurse; and sending a communication from the first physician to the first nurse in response to receiving the second selection.

Thus, some embodiments may provide rooms for a physician to choose (but not necessarily a list of patient identifiers).

Another version of Example 1 includes a method executed by at least one processor comprising: displaying to a first physician, via a display coupled to the at least one processor and at least one memory, first and second patient identifiers, wherein (a)(i) a first patient is assigned to the first patient identifier and a second patient is assigned to the second room and a second identifier, and (b)(iii) a first nurse is assigned the first patient identifier and a second nurse is assigned to the second identifier; receiving a first selection from the first physician and via the display, the first selection comprising the displayed first patient identifier; displaying a first profile of the first nurse in response to receiving the first selection; receiving a second selection, the second selection comprising a communication method from the first physician in response to displaying the first profile of the first nurse; and sending a communication from the first physician to the first nurse in response to receiving the second selection.

Thus, some embodiments may provide patient identifiers for a physician to choose (but not necessarily rooms).

Example 2

The method of example 1 comprising: displaying a first profile of the first patient in response to receiving the first selection; receiving a third selection, the third selection comprising a communication method from the first physician in response to displaying the first profile of the first patient; sending a communication from the first physician to a first family member in response to receiving the third selection; wherein the first family member is assigned to the first patient via the at least one memory.

See, for example, FIGS. 39, 40. The communication method may include messaging, as in FIG. 39. The assignment may be done with a look-up table and the like. See, e.g., FIG. 90.

See also, for example, FIG. 102 for a related embodiment.

Example 3

The method of example 2 comprising displaying the first profile of the first patient in response to receiving the first selection.

Example 4

The method of example 2 comprising: displaying first and second communication content to the first physician; receiving a fourth selection, the fourth selection comprising the first communication content; and communicating the first communication content but not the second communication content, via the communication from the first physician to the first family member, in response to receiving the fourth selection.

For example, see FIG. 40 with form messages.

Example 5

The method of example 1 comprising displaying on the map, to the first physician, a location of the first nurse in response to receiving the first selection.

See, for example, FIG. 61 showing nurses LL and TM.

Example 6

The method of example 1 comprising: receiving a third selection, the third selection comprising the second room from the first physician; displaying a second profile of the second nurse, but not displaying the first profile of the first nurse, in response to receiving the third selection; receiving a fourth selection, the fourth selection comprising a communication method from the first physician in response to displaying the second profile of the second nurse; sending a communication from the first physician to the second nurse, but not to the first nurse, in response to receiving the fourth selection.

Thus, as the physician moves through his or her rounds he or she can progress to different nurses.

Example 7

The method of example 1 wherein the communication from the first physician to the first nurse includes communication content that already existed before displaying the first profile of the first nurse.

Again, this may include "canned" or "template" communications such as those in FIG. 40. While this was shown in FIG. 40 from the nurse context the physician or other users may also use the utility.

Example 8

The method of example 7 comprising receiving a communication from the first nurse to the first physician in response to the communication from the first physician to the first nurse.

For example, see FIG. 64.

Example 9

The method of example 1 comprising: displaying the map of the hospital floor to the first nurse; displaying on the map, to the first nurse, a location of the first physician in response to sending the communication from the first physician to the first nurse.

This may help a nurse quickly locate a physician or determine how far away the physician is from the floor. For example, an embodiment may engage the physician as soon as she engages a WiFi node in the hospital lobby. The physician may then choose to start communications with nurses before the physician arrives at the floor where the nurse is located. The location of the physician would be helpful to the nurse in such a situation.

Example 10

The method of example 1 comprising: displaying a first profile of the first patient; receiving a third selection of a communication method from the first nurse in response to displaying the first profile of the first patient; sending a communication from the first nurse to a first family member in response to receiving the third selection.

See, e.g., FIG. 40.

Example 11

The method of example 1 comprising: displaying a first question to the first patient; receiving a first answer in response to displaying the first question to the first patient; and displaying a result in response to receiving the first answer.

See, e.g., FIG. 88 (or other similar questionnaire that can be used to generate results such as those of FIGS. 4-6.

Example 12

The method of example 11 comprising: displaying the first question to a second patient; receiving a second answer in response to displaying the first question to the second patient; displaying the result in response to receiving the second answer.

This shows the cumulative nature of questioning. As shown in FIGS. 4-6 a user can quickly tell if certain care taker is doing an above-par or below-par job of attending to patients. The results may be broken down by patient or, more generally, by group of patients.

Example 13

The method of example 1 comprising: displaying the map of the hospital floor to the first physician via the display, wherein the display is coupled to at least one antenna; storing the first selection in the at least one memory; and sending the communication from the first physician to the first nurse via the at least one antenna.

Example 14

The method of example 1 comprising: receiving a third selection from the first physician and via the display, the third selection comprising at least one of the displayed second room and the displayed second patient identifier; and sending a communication from the first physician to the second nurse in response to receiving the third selection.

Example 15

The method of example 14 comprising: sending the communication from the first physician to the first nurse after receiving both of the first and third selections; sending the communication from the first physician to the second nurse after receiving both of the first and third selections.

For instance, a physician may select two different rooms or patient identifiers and then send out "batch" communications to multiple nurses, residents, physicians, therapists, administrators, and the like. Thus, an attending physician may select all his or her patients to be rounded that day and then select "round with me" which is a message sent to all nurses and/or junior physicians assigned to any of the patients.

Example 16

The method of example 1 comprising simultaneously displaying on the map, to the first physician, locations of the first and second nurses before receiving the first selection.

This may occur at many different points in an embodiment. For example, this may occur as soon as a physician is detected by a WiFi node (see, e.g., FIGS. 99(A), (B), (C) for an example of a method for location tracking of user, whether the user is a doctor or any other user). Upon such detection and entering the software the physician may see a map with multiple nurses on the map, regardless of what patients those nurses may be assigned to.

Example 17

A method executed by at least one processor comprising: displaying to a first physician, via a display coupled to the at least one processor, at least one of: (a)(i) a map of a hospital floor, (a)(ii) a first patient identifier, and (a)(iii) a second patient identifier, wherein (b)(i) the map simultaneously displays first and second rooms of the hospital floor, (b)(ii) a first patient is assigned to the first room and the first patient identifier via the at least one memory, (b)(iii) a second patient is assigned to the second room and a second identifier via the at least one memory, and (b)(iv) a first nurse is assigned to the first room and the first patient identifier via the at least one memory, (b)(v) and a second nurse is assigned to the second room and the second identifier via the at least one memory; receiving a first selection from the first physician and via the display, the first selection comprising at least one of the displayed first room and the displayed first patient identifier; and sending a communication from the first physician to the first nurse, and not the second nurse, in response to receiving the first selection.

In an embodiment, a physician may not be concerned with which nurse is assigned to his or her patients. For example, a physician may simply select a group of patient identifiers and then select "round with me" to have a "round with me" communication distributed to all staff assigned to those patients—all without seeing a profile for any of the nurses.

Example 18

The method of example 17 comprising: displaying a first profile of the first nurse in response to receiving the first selection; receiving a second selection, the second selection comprising a communication method from the first physician in response to displaying the first profile of the first nurse; and sending the communication from the first physician to the first nurse in response to receiving the second selection.

Example 19

A method executed by at least one processor comprising: displaying to a first user, via a display coupled to the at least one processor and at least one memory, at least one of: (a)(i) a map of a hospital floor, (a)(ii) a first patient identifier, and (a)(iii) a second patient identifier, wherein (b)(i) the map simultaneously displays first and second rooms of the hospital floor, (b)(ii) a first patient is assigned to the first room and the first patient identifier and a second patient is assigned to the second room and a second identifier, and (b)(iii) a second user is assigned to the first room and the first patient identifier and a third user is assigned to the second room and the second identifier; receiving a first selection from the first user and via the display, the first selection comprising at least one of the displayed first room and the displayed first patient identifier; displaying a first profile of the second user in response to receiving the first selection; receiving a second selection, the second selection comprising a communication method from the first user in response to displaying the first profile of the second user; and sending a communication from the first user to the second user in response to receiving the second selection.

Thus, various examples above address specific roles for clarity (e.g., physician, nurse). However, other embodiments are not so limited and more generally concern users, such as attending physicians, residents, junior physicians, scrub technicians, therapists, nurses, orderlies, administrators, research scientists, and the like.

Example 20

The method of example 19 comprising: displaying a first profile of the first patient in response to receiving the first selection; receiving a third selection, the third selection comprising a communication method from the first user in response to displaying the first profile of the first patient; sending a communication from the first user to a third user in response to receiving the third selection; wherein the third user is assigned to the first patient via the at least one memory.

Example 21

An apparatus comprising means for performing any one of examples 1 to 20.

Example 22

A communications device arranged to carry out a method according to any one of examples 1 to 20.

Example 23

At least one machine readable medium comprising a plurality of instructions that in response to being executed on a computing device, cause the computing device to carry out a method according to any one of examples 1 to 20.

Returning to Example 1, example 1 includes a method executed by at least one processor. For example, see processor 910 of FIG. 96 (and/or processor 1310 of FIG. 98 which may work independently of the system of FIG. 96 or in cooperation as a resource constrained device that leverages utilities, such as RF transceiver 970, of resource rich system 900). The method further comprises displaying to a first physician, via a display coupled to the at least one processor and at least one memory, at least one of: (a)(i) a map of a hospital floor, (a)(ii) a first patient identifier, and (a)(iii) a second patient identifier. Such a display includes, for example, display 920 of FIG. 96. Example 1 further includes a first patient is assigned to the first room and the first patient identifier and a second patient is assigned to the second room and a second identifier. This assignment may be found in a look up table or data structure in memories 930, 935 (and/or memory 1340), and or in the cloud which is accessed via antennae 965, 990 (and/or transceiver 1390). The cloud may include servers such as the system of FIG. 97. FIG. 97 may process requests for assignments (e.g., which nurse is assigned to a patient at 10:00 a.m. on Dec. 19, 2017) using cores 1074a, 1084a to access data structures in memories 1032, 1034, 1028. The process of example 1 further includes displaying a first profile of the first nurse in response to receiving the first selection. Such a profile may be included in any of the memories described above for FIGS. 96, 97. The process of Example 1 further includes sending a communication from the first physician to the first nurse in response to receiving the second selection. Such a communication may be sent via antennae 965, 990 and WLAN transceiver 975.

While WiFi location has been addressed herein, near field communications (NFC) interface 960 and/or sensors 925 (and/or sensors 1380 and sensor hub 1320) may be utilized to indicate proximity and provide location of users to display to one another.

Figure 100:
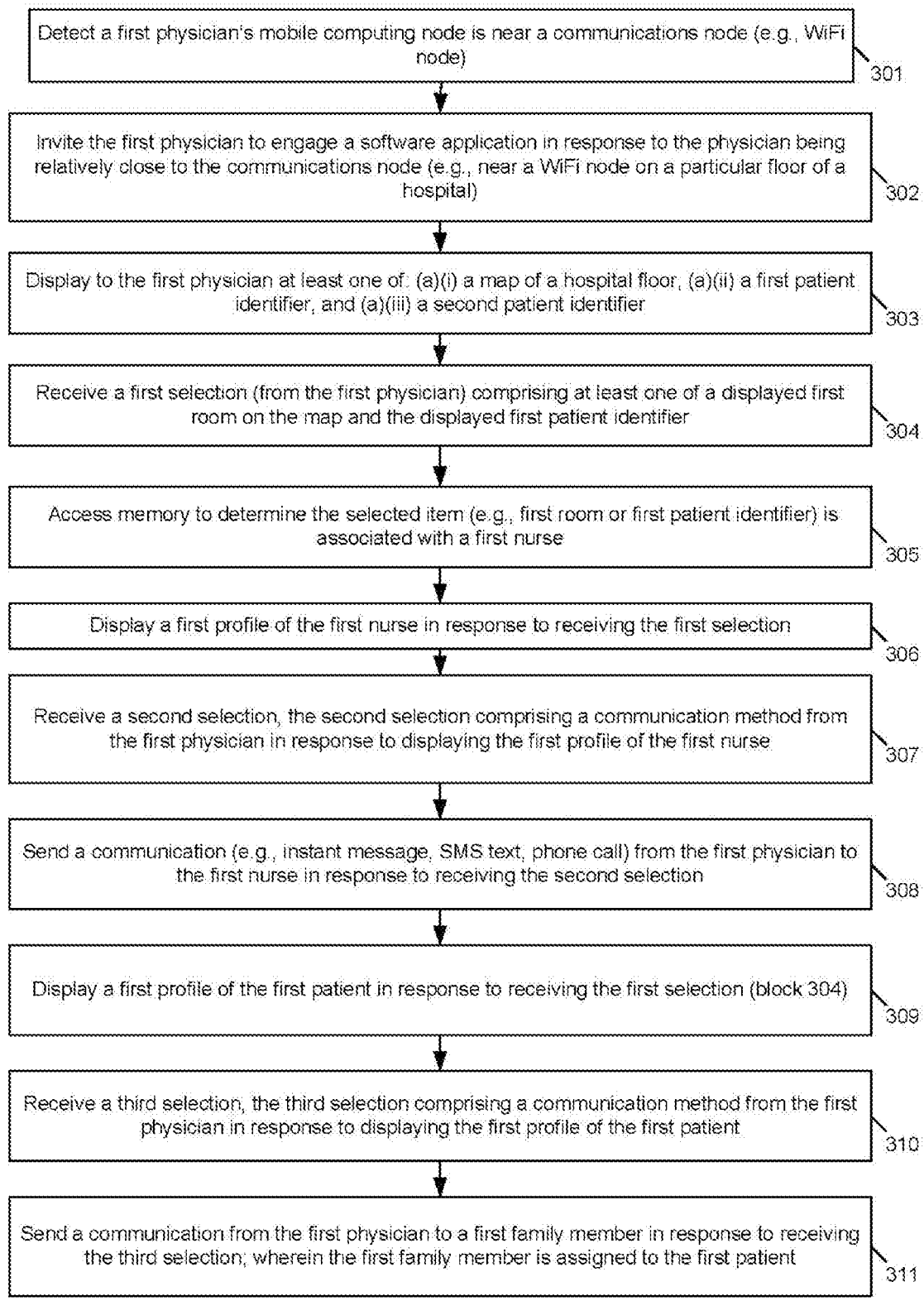
FIG. 100 includes a process in an embodiment.

In FIG. 100 an embodiment includes a process 300. Block 301 includes detecting a first physician's mobile computing node is near a communications node (e.g., WiFi node). Block 302 includes inviting the first physician to engage a software application in response to the physician being relatively close to the communications node (e.g. near a WiFi node on a particular floor of a hospital). Block 303 includes displaying to the first physician at least one of: (a)(i) a map of a hospital floor, (a)(ii) a first patient identifier, and (a)(iii) a second patient identifier. Block 304 includes receiving a first selection (from the first physician) comprising at least one of the displayed first room and the displayed first patient identifier. Block 305 includes accessing memory to determine the selected item (e.g., room or patient identifier) is associated with a first nurse. Block 306 includes displaying a first profile of the first nurse in response to receiving the first selection. Block 307 includes receiving a second selection, the second selection comprising a communication method from the first physician in response to displaying the first profile of the first nurse. Block 308 includes sending a communication (e.g., instant message, SMS text, phone call) from the first physician to the first nurse in response to receiving the second selection. Block 309 includes displaying a first profile of the first patient in response to receiving the first selection (block 304). Block 310 includes receiving a third selection, the third selection comprising a communication method from the first physician in response to displaying the first profile of the first patient. Block 311 includes sending a communication from the first physician to a first family member in response to receiving the third selection; wherein the first family member is assigned to the first patient via the at least one memory.

Other embodiments may include a subset of the steps of process 300 and/or may rearrange steps of process 300.

Example A1

A method executed by at least one processor comprising: displaying to a first physician, via a display coupled to the at least one processor and at least one memory, at least one of: (a)(i) a map of a hospital floor, (a)(ii) a first patient identifier, and (a)(iii) a second patient identifier, wherein (b)(i) the map simultaneously displays first and second rooms of the hospital floor, (b)(ii) a first patient is assigned to the first room and the first patient identifier and a second patient is assigned to the second room and a second identifier, and (b)(iii) a first nurse is assigned to the first room and the first patient identifier and a second nurse is assigned to the second room and the second identifier; receiving a first selection from the first physician and via the display, the first selection comprising at least one of the displayed first room and the displayed first patient identifier; displaying a first profile of the first nurse in response to receiving the first selection; receiving a second selection, the second selection comprising a communication method from the first physician in response to displaying the first profile of the first nurse; and sending a communication from the first physician to the first nurse in response to receiving the second selection.

Example A 2

The method of example A 1 comprising: displaying a first profile of the first patient in response to receiving the first selection; receiving a third selection, the third selection comprising a communication method from the first physician in response to displaying the first profile of the first patient; sending a communication from the first physician to a first family member in response to receiving the third selection; wherein the first family member is assigned to the first patient via the at least one memory.

Example A 3

The method of example A 2 comprising displaying the first profile of the first patient in response to receiving the first selection.

Example A 4

The method according to any of examples A 2-3 comprising: displaying first and second communication content to the first physician; receiving a fourth selection, the fourth selection comprising the first communication content; and communicating the first communication content but not the second communication content, via the communication from the first physician to the first family member, in response to receiving the fourth selection.

Example A 5

The method according to any of examples A 1-4 comprising displaying on the map, to the first physician, a location of the first nurse in response to receiving the first selection.

Example A 6

The method according to any of examples A 1-5 comprising: receiving a third selection, the third selection comprising the second room from the first physician; displaying a second profile of the second nurse, but not displaying the first profile of the first nurse, in response to receiving the third selection; receiving a fourth selection, the fourth selection comprising a communication method from the first physician in response to displaying the second profile of the second nurse; sending a communication from the first physician to the second nurse, but not to the first nurse, in response to receiving the fourth selection.

Example A 7

The method according to any of examples A 1-6 wherein the communication from the first physician to the first nurse includes communication content that already existed before displaying the first profile of the first nurse.

Example A 8

The method according to any of examples A 1-7 comprising receiving a communication from the first nurse to the first physician in response to the communication from the first physician to the first nurse.

Example A 9

The method according to any of examples A 1-8 comprising: displaying the map of the hospital floor to the first nurse; displaying on the map, to the first nurse, a location of the first physician in response to sending the communication from the first physician to the first nurse.

Example A 10

The method according to any of examples A 1, 3-5, 7-9 comprising: displaying a first profile of the first patient; receiving a third selection of a communication method from the first nurse in response to displaying the first profile of the first patient; sending a communication from the first nurse to a first family member in response to receiving the third selection.

Example A 11

The method according to any of examples A 1-10 comprising: displaying a first question to the first patient; receiving a first answer in response to displaying the first question to the first patient; and displaying a result in response to receiving the first answer.

Example A 12

The method of example A 11 comprising: displaying the first question to a second patient; receiving a second answer in response to displaying the first question to the second patient; displaying the result in response to receiving the second answer.

Example A 13

The method according to any of examples A 1-12 comprising: displaying the map of the hospital floor to the first physician via the display, wherein the display is coupled to at least one antenna; storing the first selection in the at least one memory; and sending the communication from the first physician to the first nurse via the at least one antenna.

Example A 14

The method according to any of examples A 1, 3-5, 7-9, 10-13 comprising: receiving a third selection from the first physician and via the display, the third selection comprising at least one of the displayed second room and the displayed second patient identifier; and sending a communication from the first physician to the second nurse in response to receiving the third selection.

Example A 15

The method of example A 14 comprising: sending the communication from the first physician to the first nurse after receiving both of the first and third selections; sending the communication from the first physician to the second nurse after receiving both of the first and third selections.

Example A 16

The method according to any of examples A 1-15 comprising simultaneously displaying on the map, to the first physician, locations of the first and second nurses before receiving the first selection.

Example A 17

A method executed by at least one processor comprising: displaying to a first physician, via a display coupled to the at least one processor, at least one of: (a)(i) a map of a hospital floor, (a)(ii) a first patient identifier, and (a)(iii) a second patient identifier, wherein (b)(i) the map simultaneously displays first and second rooms of the hospital floor, (b)(ii) a first patient is assigned to the first room and the first patient identifier via the at least one memory, (b)(iii) a second patient is assigned to the second room and a second identifier via the at least one memory, and (b)(iv) a first nurse is assigned to the first room and the first patient identifier via the at least one memory, (b)(v) and a second nurse is assigned to the second room and the second identifier via the at least one memory; receiving a first selection from the first physician and via the display, the first selection comprising at least one of the displayed first room and the displayed first patient identifier; and sending a communication from the first physician to the first nurse, and not the second nurse, in response to receiving the first selection.

Example A 18

The method of example A 17 comprising: displaying a first profile of the first nurse in response to receiving the first selection; receiving a second selection, the second selection comprising a communication method from the first physician in response to displaying the first profile of the first nurse; and sending the communication from the first physician to the first nurse in response to receiving the second selection.

Example A 19

A method executed by at least one processor comprising: displaying to a first user, via a display coupled to the at least one processor and at least one memory, at least one of: (a)(i) a map of a hospital floor, (a)(ii) a first patient identifier, and (a)(iii) a second patient identifier, wherein (b)(i) the map simultaneously displays first and second rooms of the hospital floor, (b)(ii) a first patient is assigned to the first room and the first patient identifier and a second patient is assigned to the second room and a second identifier, and (b)(iii) a second user is assigned to the first room and the first patient identifier and a third user is assigned to the second room and the second identifier; receiving a first selection from the first user and via the display, the first selection comprising at least one of the displayed first room and the displayed first patient identifier; displaying a first profile of the second user in response to receiving the first selection; receiving a second selection, the second selection comprising a communication method from the first user in response to displaying the first profile of the second user; and sending a communication from the first user to the second user in response to receiving the second selection.

Example A 20

The method of example A 19 comprising: displaying a first profile of the first patient in response to receiving the first selection; receiving a third selection, the third selection comprising a communication method from the first user in response to displaying the first profile of the first patient; sending a communication from the first user to a third user in response to receiving the third selection; wherein the third user is assigned to the first patient via the at least one memory.

Example A21

An apparatus comprising means for performing any one of examples A 1 to 20.

Example A 22

A communications device arranged to carry out a method according to any one of examples A 1 to 20.

Example A 23

At least one machine readable medium comprising a plurality of instructions that in response to being executed on a computing device, cause the computing device to carry out a method according to any one of examples A 1 to 20.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. At least one non-transitory machine-readable medium having stored thereon data which, if used by at least one machine, causes the at least one machine to perform operations comprising:
    displaying to a physician, via a display, a map of a hospital floor, wherein (a) the map simultaneously displays first and second rooms of the hospital floor, (b) a first patient is assigned to the first room and a first patient identifier and a second patient is assigned to the second room and a second patient identifier, (c) a first nurse is assigned to the first room and the first patient identifier and a second nurse is assigned to the second room and the second patient identifier, and (d) the first and second nurses are not the same person;
    receiving a first selection from the physician and via the display, the first selection comprising at least one of the displayed first room or a display of the first patient identifier;
    receiving a second selection from the physician and via the display, the second selection comprising at least one of the displayed second room and a display of the second patient identifier;
    receiving a third selection from the physician and via the display, the third selection comprising a graphical user interface element to initiate a batch communication;
    sending a first communication from the physician to the first nurse in response to receiving the first and third selections; and sending a second communication from the physician to the second nurse in response to receiving the second and third selections;

wherein the first and second communications are included in a batch communication with one another, the batch communication occurring after the first, second, and third selections are received and in response to the first, second, and third selections.

2. The at least one medium of claim 1 having stored thereon data which, if used by the at least one machine, causes the at least one machine to perform operations comprising:

displaying a first profile of the first patient in response to receiving the first selection;

receiving a fourth selection, the fourth selection comprising a communication method from the physician in response to displaying the first profile of the first patient;

sending a third communication from the physician to a first family member in response to receiving the fourth selection;

wherein the first family member is assigned to the first patient.

3. The at least one medium of claim 1 having stored thereon data which, if used by the at least one machine, causes the at least one machine to perform operations comprising displaying a first profile of the first patient in response to receiving the first selection.

4. The at least one medium of claim 2 having stored thereon data which, if used by the at least one machine, causes the at least one machine to perform operations comprising:

displaying first and second communication content to the physician;

receiving a fifth selection, the fifth selection comprising the first communication content; and communicating the first communication content but not the second communication content, via the third communication from the physician to the first family member, in response to receiving the fifth selection.

5. The at least one medium of claim 1 having stored thereon data which, if used by the at least one machine, causes the at least one machine to perform operations comprising displaying:

(a) a first profile of the first nurse in response to receiving the first selection, and (b) a location of the first nurse on the map in response to receiving the first selection.

6. The at least one medium of claim 5 wherein the first communication from the physician to the first nurse includes communication content that already existed before displaying the first profile of the first nurse.

7. The at least one medium of claim 1 having stored thereon data which, if used by the at least one machine, causes the at least one machine to perform operations comprising receiving a communication from the first nurse to the physician in response to the first communication from the physician to the first nurse.

8. The at least one medium of claim 1 having stored thereon data which, if used by the at least one machine, causes the at least one machine to perform operations comprising:

displaying the map of the hospital floor to the first nurse;

displaying on the map, to the first nurse, a location of the physician in response to sending the first communication from the physician to the first nurse.

9. The at least one medium of claim 8 having stored thereon data which, if used by the at least one machine, causes the at least one machine to perform operations comprising:

displaying a first profile of the first patient;

receiving a fourth selection of a communication method from the first nurse in response to displaying the first profile of the first patient;

sending a third communication from the first nurse to a first family member in response to receiving the fourth selection.

10. The at least one medium of claim 1 having stored thereon data which, if used by the at least one machine, causes the at least one machine to perform operations comprising:

displaying a first question to the first patient;

receiving a first answer in response to displaying the first question to the first patient; and displaying a result in response to receiving the first answer.

11. The at least one medium of claim 10 having stored thereon data which, if used by the at least one machine, causes the at least one machine to perform operations comprising:

displaying the first question to a second patient;

receiving a second answer in response to displaying the first question to the second patient;

displaying the result in response to receiving the second answer.

12. The at least one medium of claim 1 having stored thereon data which, if used by the at least one machine, causes the at least one machine to perform operations comprising:

displaying the map of the hospital floor to the physician via the display, wherein the display is coupled to at least one antenna;

storing the first selection in the at least one medium; and sending the first communication from the physician to the first nurse via the at least one antenna.

13. The at least one medium of claim 1 having stored thereon data which, if used by the at least one machine, causes the at least one machine to perform operations comprising simultaneously displaying on the map, to the physician, locations of the first and second nurses before receiving the first selection.

14. The at least one medium of claim 1 having stored thereon data which, if used by the at least one machine, causes the at least one machine to perform operations comprising, after the first nurse is assigned to the first room and the first patient identifier, receiving the first and third selections without having already displayed a first profile of the first nurse.

* * * * *